(12) United States Patent
Hecker et al.

(10) Patent No.: US 10,385,074 B2
(45) Date of Patent: Aug. 20, 2019

(54) SYNTHESIS OF BORONATE SALTS AND USES THEREOF

(71) Applicant: Rempex Pharmaceuticals, Inc., Lincolnshire, IL (US)

(72) Inventors: Scott Hecker, Del Mar, CA (US); Serge Boyer, San Diego, CA (US)

(73) Assignee: REMPEX PHARMACEUTICALS, INC., Lincolnshire, IL (US)

( * ) Notice: Subject to any disclaimer, the term of this patent is extended or adjusted under 35 U.S.C. 154(b) by 28 days.

(21) Appl. No.: 15/305,954

(22) PCT Filed: Apr. 30, 2015

(86) PCT No.: PCT/US2015/028613
§ 371 (c)(1),
(2) Date: Oct. 21, 2016

(87) PCT Pub. No.: WO2015/171430
PCT Pub. Date: Nov. 12, 2015

(65) Prior Publication Data
US 2017/0057979 A1    Mar. 2, 2017

Related U.S. Application Data

(60) Provisional application No. 61/988,690, filed on May 5, 2014.

(51) Int. Cl.
G07F 5/02 (2006.01)
C07F 5/02 (2006.01)
A01N 55/08 (2006.01)

(52) U.S. Cl.
CPC .............. *C07F 5/025* (2013.01); *A01N 55/08* (2013.01)

(58) Field of Classification Search
CPC .................................................... C07F 5/025
See application file for complete search history.

(56) References Cited

U.S. PATENT DOCUMENTS

| | | | |
|---|---|---|---|
| 4,194,047 A | 3/1980 | Christensen et al. |
| 4,260,543 A | 4/1981 | Miller |
| 4,409,214 A | 10/1983 | Takaya et al. |
| 4,822,786 A | 4/1989 | Zama et al. |
| 5,442,100 A | 8/1995 | Bjorkquist et al. |
| 5,888,998 A | 3/1999 | Maiti et al. |
| 6,184,363 B1 | 2/2001 | Shoichet et al. |
| 6,586,615 B1 | 7/2003 | Kettner et al. |
| 7,271,186 B1 | 9/2007 | Shoichet et al. |
| 7,439,253 B2 | 10/2008 | Lampilas et al. |
| 7,582,621 B2 | 9/2009 | Baker et al. |
| 7,612,087 B2 | 11/2009 | Aszodi et al. |
| 8,680,136 B2 | 3/2014 | Hirst et al. |
| 9,012,491 B2 | 4/2015 | Reddy et al. |
| 9,101,638 B2 | 8/2015 | Reddy et al. |
| 9,132,140 B2 | 9/2015 | Reddy et al. |
| 9,156,858 B2 | 10/2015 | Reddy et al. |
| 9,296,763 B2 | 3/2016 | Hirst et al. |
| 9,511,142 B2 | 12/2016 | Burns et al. |
| 2004/0019203 A1 | 1/2004 | Micetich et al. |
| 2004/0157826 A1 | 8/2004 | Lampilas et al. |
| 2005/0020572 A1 | 1/2005 | Aszodi et al. |
| 2006/0019116 A1 | 1/2006 | Conley et al. |
| 2006/0178357 A1 | 8/2006 | Buynak et al. |
| 2006/0210883 A1 | 9/2006 | Chen et al. |
| 2010/0056478 A1 | 3/2010 | Desarbre et al. |
| 2010/0120715 A1 | 5/2010 | Burns et al. |
| 2010/0256092 A1 | 10/2010 | Xia et al. |
| 2011/0288063 A1 | 11/2011 | Maiti et al. |
| 2012/0040932 A1 | 2/2012 | Hirst et al. |
| 2013/0316978 A1 | 11/2013 | Reddy et al. |
| 2013/0331355 A1 | 12/2013 | Griffith et al. |
| 2013/0345172 A1 | 12/2013 | Hirst et al. |
| 2014/0194284 A1 | 7/2014 | Reddy et al. |
| 2014/0194381 A1 | 7/2014 | Reddy et al. |
| 2014/0194382 A1 | 7/2014 | Reddy et al. |
| 2014/0194385 A1 | 7/2014 | Reddy et al. |
| 2014/0194386 A1 | 7/2014 | Burns et al. |
| 2014/0206648 A1 | 7/2014 | Reddy et al. |
| 2015/0119363 A1 | 4/2015 | Dudley et al. |
| 2016/0220591 A1 | 8/2016 | Hirst et al. |
| 2016/0339045 A1 | 11/2016 | Griffith et al. |

FOREIGN PATENT DOCUMENTS

| | | |
|---|---|---|
| EP | 1550657 A1 | 7/2005 |
| EP | 2508506 A1 | 10/2012 |
| FR | 2573070 A1 | 5/1986 |
| JP | 2003-229277 | 8/2003 |
| JP | 2004-291253 | 10/2004 |
| WO | WO 1987/05297 | 9/1987 |
| WO | WO 1989/10961 | 11/1989 |

(Continued)

OTHER PUBLICATIONS

International Search Report and Written Opinion dated Aug. 17, 2015 for International Application No. PCT/US2015/028613, filed Apr. 30, 2015.

Abdel-Magid et al., "Reductive Amination of Aldehydes and Ketones with Sodium Triacetoxyborohydride: Studies on Direct and Indirect Reductive Amination Procedures", J Org Chem. (1996) 61(11):3849-3862.

Adediran et al., "A 'cephalosporin-like' cyclic depsipeptide: Synthesis and reaction with beta-lactam-recognizing enzymes", Bioorg Med Chem Lett. (1999) 9(3):341-346.

Aizpurua et al., "Synthesis of benzyl halides from aldehydes promoted by halosilanes and 1,1,3,3-tetramethyldisiloxane (TMDS)", Tetrahedron Lett. (1984) 25(10):1103-1104.

(Continued)

*Primary Examiner* — Shawquia Jackson
(74) *Attorney, Agent, or Firm* — Wilmer Cutler Pickering Hale and Dorr LLP

(57) ABSTRACT

Disclosed herein are boronate intermediates in the synthesis of antimicrobial compounds and the use and preparation thereof. Some embodiments relate to crystalline boronate salt derivatives and their use in the synthesis of therapeutic compounds.

26 Claims, No Drawings

(56) References Cited

FOREIGN PATENT DOCUMENTS

| | | |
|---|---|---|
| WO | WO 1998/56392 A1 | 12/1998 |
| WO | WO 2000/035904 A1 | 6/2000 |
| WO | WO 2000/035905 A1 | 6/2000 |
| WO | WO 2001/023374 A1 | 4/2001 |
| WO | WO 2001/030149 | 5/2001 |
| WO | WO 2002/022137 A1 | 3/2002 |
| WO | WO 2002/083884 | 10/2002 |
| WO | WO 2003/070714 | 8/2003 |
| WO | WO 2004/039859 | 5/2004 |
| WO | WO 2004/058679 A2 | 7/2004 |
| WO | WO 2004/064755 A2 | 8/2004 |
| WO | WO 2005/033090 | 4/2005 |
| WO | WO 2005/035532 A1 | 4/2005 |
| WO | WO 2005/087700 | 9/2005 |
| WO | WO 2006/052733 A1 | 5/2006 |
| WO | WO 2006/091771 | 8/2006 |
| WO | WO 2007/058602 A2 | 5/2007 |
| WO | WO 2007/065288 A2 | 6/2007 |
| WO | WO 2007/095638 | 8/2007 |
| WO | WO 2008/039420 A2 | 4/2008 |
| WO | WO 2008/116813 A1 | 10/2008 |
| WO | WO 2009/046098 A1 | 4/2009 |
| WO | WO 2009/064413 A1 | 5/2009 |
| WO | WO 2009/064414 A1 | 5/2009 |
| WO | WO 2009/091856 A1 | 7/2009 |
| WO | WO 2009/117540 A1 | 9/2009 |
| WO | WO 2009/139834 A1 | 11/2009 |
| WO | WO 2009/140309 A2 | 11/2009 |
| WO | WO 2010/056827 A1 | 5/2010 |
| WO | WO 2010/075286 A1 | 7/2010 |
| WO | WO 2010/097675 A1 | 9/2010 |
| WO | WO 2010/130708 A1 | 11/2010 |
| WO | WO 2010/144338 A1 | 12/2010 |
| WO | WO 2011/017125 A1 | 2/2011 |
| WO | WO 2011/103686 A1 | 9/2011 |
| WO | WO 2011/123502 A1 | 10/2011 |
| WO | WO 2012/021455 | 2/2012 |
| WO | WO 2012/058065 A1 | 5/2012 |
| WO | WO 2012/067664 A1 | 5/2012 |
| WO | WO 2012/106995 A1 | 8/2012 |
| WO | WO 2012/136383 A1 | 10/2012 |
| WO | WO 2013/033461 A1 | 3/2013 |
| WO | WO 2013/053372 A1 | 4/2013 |
| WO | WO 2013/056163 A1 | 4/2013 |
| WO | WO 2013/092979 A1 | 6/2013 |
| WO | WO 2013/104774 A1 | 7/2013 |
| WO | WO 2013/104897 A1 | 7/2013 |
| WO | WO 2013/122888 | 8/2013 |
| WO | WO 2013/184845 A1 | 12/2013 |
| WO | WO 2014/089365 A1 | 6/2014 |
| WO | WO 2014/107535 A1 | 7/2014 |
| WO | WO 2014/107536 A1 | 7/2014 |
| WO | WO 2014/110442 A1 | 7/2014 |
| WO | WO 2014/151958 A1 | 9/2014 |
| WO | WO 2015/171398 A1 | 11/2015 |
| WO | WO 2015/179308 A1 | 11/2015 |
| WO | WO 2016/003929 A1 | 1/2016 |
| WO | WO 2016/065282 A1 | 4/2016 |

OTHER PUBLICATIONS

Akiyama et al., "N-Hydroxy Amides. Part 6. Synthesis and Spectroscopic Properties of 1-Hydroxypiperazine-2,5-diones", J Chem Soc., Perkin Trans I, (1989) 2:235-239.
Allen et al., "Ansel's Pharmaceutical Dosage Forms and Drug Delivery Systems", 8th Edition (2004) TOC only.
American Chemical Society. STN Chemical Database Registry RN: 1226917; Jun. 2010; 2 pages.
Arya et al., "Advances in asymmetric enolate methodology", Tetrahedron (2000) 56:917-947.
Babic et al., "What's new in antibiotic resistance? Focus on beta-lactamases", Drug Res Updates (2006) 9:142-156.
Bassetti et al., "New antibiotics for bad bugs: where are we?", Ann Clin Microbiol Antimicrob. (2013) 12:22-36.
Becker, Daniel E., "Antimicrobial Drugs", Anesth Prog (2013) 60:111-123.
Beenen et al., "Asymmetric copper-catalyzed synthesis of alpha-amino boronate esters from N-tert-butanesulfinyl aldimines", J Am Chem Soc. (2008) 130(22):6910-6911.
Biedrzycki et al., "Derivatives of tetrahedral boronic acids", J. Organomet. Chem. (1992) 431:255-270.
Bou et al., "Cloning, nucleotide sequencing, and analysis of the gene encoding an AmpC beta-lactamase in Acinetobacter baumannii", Antimicrob Agents Chemother (2000) 44(2):428-432.
Bou et al., "OXA-24, a novel class D beta-lactamase with carbapenemase activity in an Acinetobacter baumannii clinical strain", Antimicrob Agents Chemother (2000) 44(6):1556-1561 and Erratum: Antimicrob Agents Chemother. (2006) 50(6) 2280.
Brabez et al., "Design,synthesis, and biological studies of efficient multivalent melanotropin ligands: tools toward melanoma diagnosis and treatment", J Med Chem. (2011) 54(20):7375-7384.
Brosz et al., "Resolution of alpha-aminoboronic esters by diastereoselective crystallization with pinanediols. Confirmation by x-ray analysis", Tetrahedron: Asymmetry (1997) 8(9):1435-1440.
Bush et al., "Minireview: Updated Functional Classification of beta-Lactamases," Antimicrob Agents Chemo. (2010) 54(3):969-976.
CAS Registry Nos. 69190-59/60 (2-(bis(phenylthio)methyl)-4,4,5,5-tetramethyl-1,3,2-dioxaborolane) and 69190-60-9 (2-(bis(phenylthio)methyl)-1,3,2-dioxaborinane) Scheme 18 (2015); 2 pages.
CAS Registry No. 105892-95-3 Boronic acid [1-(phenylsulfonyl)heptyl]-, dimethyl ester (2015); 2 pages.
Cheng et al., "Synthesis of Aryl Thioethers through the N-Chlorosuccinimide-Promoted Cross-Coupling Reaction of Thiols with Grignard Reagents", J Org Chem. (2012) 177(22):10369-10374.
Chemicalland21.com. "Meglumine", Jun. 7, 2011. Downloaded from </www.chemicalland21.com/lifescience/phar/N-METHYL-D-GLUCAMINE.htm>; 2 pages.
Clinical and Laboratory Standards Institute (formerly NCCLS, National Committee for Clinical Laboratory Standards). "Methods for Dilution of Antimicrobial Susceptibility Tests for Bacteria That Grow Aerobically", CLSI (Jan. 2006) M7-A7 26(2), 64 pages.
Clinical and Laboratory Standards Institute (formerly NCCLS, National Committee for Clinical Laboratory Standards). "Methods for Dilution of Antimicrobial Susceptibility Tests for Bacteria That Grow Aerobically", CLSI (Jan. 2009) M07-A8 29(2), 88 pages.
Clinical Trial NCT02168946, "A Phase 3, Multi-Center, Randomized, Open-Label Study of Carbavance (Meropenem/RPX7009) Versus Best Available Therapy in Subjects with Selected Serious Infecations Due to Carbapenem-Resistant Enterobacteriaceae", 6. Oct. 12014; retrieved online from URL:https://clincaltrials.gov/archive/NCT02168946/20140_10_06.
Conte et al., "Intrapulmonary pharmacokinetics and pharmacodynamics of meropenem", Int J Antimicrob Agents (Dec. 2005) 26(6):449-456.
Coppa et al., "A Facile, Convenient and Selective Homolytic Carbamolylation of Heteroaromatic Bases", Heterocycles (1993) 36(12):2687-2696.
Coutts et al., "Two Efficient Methods for the Cleavage of Pinanediol Boronate Esters Yielding the Free Boronic Acids", Tetrahedron Lett. (1994) 35(29):5109-5112.
Danziger et al., "Automated Site-directed Drug Design: A General Algorithm for Knowledge Acquisition about Hydrogen-bonding Regions at Protein Surfaces", Proc. Royal Soc London, Series B, Biol. Sciences (1989) 236(1283):101-113.
Darses et al., "Potassium Organotrifluoroborates: New Perspectives in organic Synthesis", Chem Rev. (2008) 108:288-325.
Davoli et al., "Enantioselective total synthesis of (−)-microcarpalide", Tetrahedron (2005) 61:4427-4436.
De Meijere A. [Ed], Science of Synthesis—vol. 24; "Three Carbon-Heteroatom Bonds: Ketene Acetals and Yne-X Compounds", TOC 46 pages.
Di Gioia et al., "Optically Pure N-Hydroxy-O-triisopropylsilyl-alpha-L-amino Acid Methyl Esters from AlCl3-Assisted Ring Open-

(56) References Cited

OTHER PUBLICATIONS ing of Chiral Oxaziridines by Nitrogen Containing Nucleophiles", J Org Chem. (2005) 70(25):10494-10501.
Drawz et al., "Three Decades of beta-Lactamase Inhibitors", Clin Microbiol Reviews (Jan. 2010) 23(1):160-201.
Eidam et al., "Design, synthesis, crystal structures and antimicrobial activity of sulfonamide boronic acids as beta-lactamase inhibitors", J Med Chem. (2010) 53(21):7852-7863.
Eissenstat et al., "Aminoalkylindoles: Structure-Activity Relationships of Novel Cannabinoid Mimetics", J Med Chem. (1995) 38(16):3094-3105.
El Nezhawy et al., "Synthesis and antioxidant activity of some thiazolidin-4-one derivatives", Springer; Chemical Monthly/ Monatshefte für Chemie (2009) 140(5):531-539.
Endo et al., "Chemoselective Suzuki coupling of diborylmethane for facile synthesis of benzylboronates", Org Lett. (2011) 13(13):3368-3371.
Fan, et al. (2009): STN International HCAPLUS database, Columbus (OH), accession No. 2009: 425839; 6 pages.
Farquhar et al., "Intensely potent doxorubicin analogues: structure-activity relationship", J. Med. Chem. (1998) 41(6):965-972.
Ghosh et al., "Enantioselective total synthesis of (+)-largazole, a potent inhibitor of histone deacetylase", Org Lett. (2008) 10(17):3907-3909.
Giroux, A., "Synthesis of benzylic boronates via palladium-catalyzed cross-coupling reaction of bis(pinacolato)diboron with benzylic halides", Tetrahedron Lett. (2003) 44:233-235.
Gorovoy et al., "Boron-Containing Peptidomimetics—A Novel Class of Selective Anti-tubercular Drugs", Chem Biol Drug Des. (Jan. 2013) 81(3):408-413.
Gossinger et al., "Towards EPC-syntheses of the structural class of cochleamycins and macquarimicins. Part 3: EPC-syntheses of the beta-keto lactone subunits and first attempts towards the syntheses of the pentacyclic antibiotics of this group", Tetrahedron (2007) 163:8336-8350.
Graham et al., "D is for Drugs", Chemistry & Industry, Mar. 19, 2013, pp. 28-30, Downloaded from http://www.concertpharma.com/wp-content/uploads/2014/12/ChemistryIndustry-0313.pdf; 3 pages.
Greene, et al., *Greene's Protective Groups in Organic Synthesis*, 4th Edition, (2007); pp. 774, 785 & 787.
Hama et al., "Palladium-Catalyzed alpha-Arylation of Zinc Enolates of Esters: Reaction Conditions and Substrate Scope", J Org Chem. (2013) 78(17):8250-8266.
Hecker et al., "Discovery of a Cyclic Boronic Acid beta-Lactamase Inhibitor (RPX7009) with Utility vs Class A Serine Carbapenemases", J Med Chem. (Mar. 2015) 58:3682-3692.
Imanishi et al., "Discovery of a Novel Series of Biphenyl Benzoic Acid Derivatives as Potent and Selective Human beta3-Adrenergic Receptor Agonists with Good Oral Bioavailability. Part I", J Med Chem. (2008) 51(6):1925-1944.
Inglis et al., "Observations on the Deprotection of Pinanediol and Pinacol Boronate Esters via Fluorinated Intermediates", J Org Chem. (2010) 75(2):468-471.
Ishii et al, "In vitro potentiation of carbapenems with ME1071, a Novel metallo-β-lactamase inhibitor, against metallo-βlactamase producing pseudomonas aeruginosa clinical isolates." Antimicrob. Agents Chemother. doi:10.1128/AAC.01397-09 (2010) 54(9):3625-3629.
Ito et al., "An efficient constructive method for a tricyclic system: an important intermediate for the synthesis of tricycloclavulone", Tetrahedron Lett. (2003) 44:1259-1261.
Jadhav et al., "Direct synthesis of [alpha-[(tert-Butoxycarbonyl)amino]alkyl]-boronates from (alpha-Haloalkyl)boronates", Org Chem. (1996) 61(22):7951-7954.
Jagannathan et al., "Synthesis of Boronic Acid Analogues of alpha-Amino Acids by Introducing Side Chains as Electrophiles", J Org Chem. (2001) 66(19):6375-6380.
Jiang et al., "A Practical Synthesis of Cefcapene Pivoxil", Synthesis (2012) 44:207-214.
Johnson et al., "A drug targeting motif for glycosidase inhibitors: An iminosugar-boronate shows unexpectedly selective beta-galactosidase inhibition", Tetrahed Lttrs. (2002) 43(49):8905-8908.
Kabalka et al., "Synthesis of a series of bornonated unnatural cyclic amino acids as potential boron neutron capture therapy agents", Appl Organomet Chem. (2008) 22(9):516-522.
Kanai et al., "Synthesis of ortho-Acylbenzylboronates via Cross-Coupling Reaction of (Dialkoxyboryl)methylzinc Reagents with Haloarenes. A Stable ortho-Quinodimethane Precursor", Chem Letts. (1993) 22(5):845-848.
Kawamorita et al., "Synthesis of Primary and Secondary Alkylboronates through Site-Selective C(sp3)-H Activation with Silica-supported Monophosphine-Ir Catalysts", J Am Chem Soc. (2013) 135(8):2947-2950.
Kikuchi et al., "Comparison of the Pharmacodynamics of Biapenem in Bronchial Epithelial Lining Fluid in Healthy Volunteers Given Half-Hour and Three-Hour Intravenous Infusions", Antimicrob Agents Chemother. (Jul. 2009) 53(7):2799-2803.
Kint et al., "New-found fundamentals of bacterial persistence", Trends Microbiol. (2012) 20(12):577-585.
Kose et al., "Synthesis of photochromic 2,3-bis(5-methyl-2-phenyl-4-thiazolyl)-1,4-naphthoquinone derivatives", J Photochem Photobiol. A: Chemistry. (2011) 219(1):58-61.
Kotha et al., "Recent applications of the suzuki-miyaura cross-coupling reaction in organic synthesis", Tetrahedron (2002) 58:9633-9695.
Kumar et al., "Synthesis of intermediates for the lactone moiety of mevinic acids via tellurium chemistry", J. Org. Chem., (1994) 59(17):4760-4764.
Kumar et al., "Development of Practical Methodologies for the Synthesis of Functionalized Benzoboroxoles", Tetrahedron Lett. (Aug. 25, 2010) 51(34):4482-4485.
Kusakabe et al., "Preparation of Optically Acitve 2-Furylcarbinols by Kinetic Resolution Using the Sharpless Reagent and Their Application in Organic Synthesis", J org Chem (1989) 54(9):2085-2091.
Kuti et al., "Use of Monte Carlo simulation to design an optimized pharmacodynamic dosing strategy for meropenem", J Clin Pharmacol. (Oct. 2003) 43(10:1116-1123.
Laitar et al., "Catalytic diboration of aldehydes via insertion into the copper-boron bond", J Am Chem Soc. (2006) 128(34):11036-11037.
Lapuebla et al., "Activity of Meropenem Combined with RPX7009, a Novel beta-Lactamase Inhibitor, against Gram-Negative Clinical Isolates in New York City", Antimicrob Agents Chemother. (Aug. 2015) 59(8):4856-4860.
Lee et al., "Vicinal Diboronates in High Enantiomeric Purity through Tandem Site-Selective NHC-Cu-Catalyzed Boron-Copper Additions to Terminal Alkynes", J Am Chem Soc. (Dec. 2009) 131(51):18234-18235.
Li et al, "Novel macrocyclic HCV NS3 protease inhibitors derived from α-amino cyclic boronates", Bioorganic Med Chem Lett. (2010) 20:5695-5700.
Li et al., "Synthesis and evaluation of novel alpha-amino cyclic boronates as inhibitors of HCV NS3 protease", Bioorg Med Chem Lett. (2010) 20:3550-3556.
Li et al., "Stereoselective total synthesis of etnangien and etnangien methyl ester", J Org Chem. (2010) 75(8):2429-2444.
Liang et al., "The Efficient Copper(I) (Hexabenzyl)tren Catalyst and Dendritic Analogues for Green "Click" Reactions between Azides and Alkynes in Organic Solvent and in Water: Positive Dendritic Effects and Monometallic Mechanism", Advance Syn Catal. (2011) 353(18): 3434-3450.
Lima et al., "Bioisosterism: A Useful Strategy for Molecular Modification and Drug Design", Curr Med Chem. (2005) 12:23-49.
Liu et al., "Selective Protein tyrosine phosphatase 1B inhibitors: Targeting the second phosphotyrosine binding site with non-carboxylic acid-containing ligands", J Med Chem. (2003) 46(16):3437-3440.
Liu et al., "Application of Stereoselective Ether Transfer to the Synthesis of Isotactic Polyethers", J Org Chem. (2010) 75(12):3953-3957.

(56) References Cited

OTHER PUBLICATIONS

Livermore et al., "Activities of NXL104 combinations with Ceftazidime and Aztreonam against Carbapenemase-producing Enterobacteriaceae", Antimicr Agents Chemother. (2011) 55(1):390-394.
Livermore, et al., "Activity of biapenem (RPX2003) combined with the boronate beta-lactamase inhibitor RPX7009 against carbapenem-resistant Enterobacteriaceae", J Antimicrob Chemother. (Aug. 2013) 68(8):1825-1831.
Lodise et al., "Penetration of meropenem into epithelial lining fluid of patients with ventilator-associated pneumonia", Antimicrob Agents Chemother. (Apr. 2011) 55(4):1606-1610.
Malfertheiner et al., "Current concepts in the management of Helicobacter pylori infection: the Maastricht III Consensus Report", Gut (2007) 56(6):772-781.
Matteson et al., "Iodomethaneboronic Esters and Aminomethaneboronic Esters", J Organomet. Chem. (1979) 170:259-264.
Matteson et al., "A Directed Chiral Synthesis of Amino Acids from Boronic Esters", Tetrahedron Lett. (1987) 28(39):4499-4502.
Matteson, D.S., "Asymmetric Synthesis with Boronic Esters", Acc Chem Res. (1988) 21(8):294-300.
Matteson, "Boronic esters in stereodirected synthesis", Tetrahedron (1989) 45(7):1859-1885.
Matteson et al., "A stereospecific convergent coupling of nucleophilic and electrophilic chiral carbons", J. Am. Chem. Soc. (1989) 111:4399-4402.
Matteson et al., "Synthesis of asymmetrically deuterated glycerol and dibenzylglyceraldehyde via boronic esters", J. Am. Chem. Soc. (1990) 112:3964-3969.
Matteson et al., "(Alkoxyalkyl)boronic Ester Intermediates for Asymmetric Synthesis", Organometallics (1996) 15:152-163.
Matteson, "Alpha-Halo Baronic Esters in Asymmetric Synthesis", Tetrahedron (1998) 54(36):10555-10607.
Matteson et al., "Glass-Catalyzed Conversion of Boronic Esters of Asymmetric Diols to Diol Sulfites and Amine Complexes of Boron Halides", Oranometallics (2001) 20(13):2920-2923 & supporting Information (9 pages).
Matteson et al., "Cesium Alkyltrifluoroborates from Asymmetric Boronic Esters", Synlett (Jul. 2006) 20:3501-3503.
Matteson et al., "Synthesis of a (Beta-acetamido-alpha-acetoxyethyl) boronic ester via azido boronic esters", J Organomet Chem. (2008) 693:2258-2262.
Meanwell, "Synopsis of some recent tactical application of bioisosteres in drug design", J. Med. Chem. (2011) 54:2529-2591.
Mendoza et al., "Bis(phenylthio)methaneboronic Esters as Sources of Carbanions and Ketene Thioacetals", J Org Chem. (1979) 44(8):1352-1354.
Micalizio et al., "A Boronic Ester Annulation Strategy for Diversity-Oriented Organic Synthesis", Angew Chem Int Ed Engl. (2002) 41(1):152-154.
Montalbetti et al., "Amide bond formation and peptide coupling", Tetrahedron (2005) 61:10827-10852.
Montefour et al., "Acinetobacter baumannii: an emerging multidrug-resistant pathogen in critical care", Crit Care Nurse (2008) 28(1):15-25.
Morandi et al., "Structure-based optimization of cephalothin-analogue boronic acids as beta-lactamase inhibitors", Bioorg Med Chem. (2008) 16(3):1195-205. Epub Nov. 7, 2007.
Nema et al., "Excipients and Their Role in Approved Injectable Products: Current Usage and Future Directions", PDA J Pharm Sci Technol. (2011) 65(3):287-332.
Ness et al., "Structure-based design guides the improved efficacy of deacylation transition state analogue inhibitors of TEM-1 beta-Lactamase", Biochemistry (2000) 39(18):5312-5321.
Nordmann et al., How to Detect NDM-1 Producers, J. Clin. Micro. (2011) 49:718-721.
Panek et al., "Diastereoselectivity in the borane methyl sulfide promoted hydroboration of .alpha.-alkoxy-.beta, gamma.-unsaturated esters. Documentation of an alkoxy-directed hydroboration reaction", J. Org. Chem. (1992) 57(20):5288-5290.

Patani et al., "Bioisosterism: A Rational Approach in Drug Design", Chem Rev. (1996) 96:3147-3176.
Paterson et al., "Extended-Spectrum beta-Lactamases: a Clinical Update", Clin Microbiol Rev. (2005) 18(4):657-686.
Perez et al., "Why are we afraid of Acinetobacter baumannii?", Expert Rev Anti Infect Ther. (2008) 6(3):269-71.
Pintaric et al., "An Opportunity for Mg-Catalyzed Grignard-Type Reactions: Direct Coupling of Benzylic Halides with Pinacolborane with 10 mol % of Magnesium", J Am Chem Soc. (2010) 132(34): 11825-11827.
Powell et al., "Compendium of excipients for parenteral formulations", PDA J Pharm Sci Technol. (1998) 52(5):238-311.
Reissig et al., "High diastereoselection in the alkylation of siloxy-substituted methyl cyclopropanecarboxylates: consequence of a pyramidal ester enolate anion?", J. Am. Chem. Soc. (1982) 104:1735-1737.
Robak et al., "Synthesis and applications of tert-butanesulfinamide", Chem Rev. (2010) 110(6):3600-3740.
Rodriguez-Martinez et al., "VIM-19, a Metallo-beta-lactamase with increased Carbapenemase Activity from *Escherichia coli* and Klebsiella pneumoniae", Antimicro Agents Chemother. (2010) 54(1):471-476.
Sabet et al., "In Vivo Efficacy of Carbavance (Meropenem/RPX7009) Against KPC-Producing Enterobacteriaceae", Abstracts of the 54th Interscience Conference on Antimicrobial Agents and Chemotherapy (Sep. 5-9, 2014) F-958; 3 pages.
Sawyer et al., "Physical properties and synthetic utility of a-alkoxyorganolithium species as studied through ligand selectivity in tin-lithium exchange", J. Am. Chem. Soc. (1988) 110:842-853.
Selander et al., "Palladium-catalyzed allylic C—OH functionalization for efficient synthesis of functionalized allylsilanes", J Am Chem Soc. (2011) 133(3):409-411.
Shaffer, Robyn Kroop, "The Challenge of Antibiotic-Resistant *Staphylococcus*: Lessons from Hospital Nurseries in the mid-20th Century", Yale J Biol Med. (2013) 86:261-270.
Shao et al., "Asymmetric hydrogenation of 3,5-Dioxoesters catalyzed by Ru-binap complex: A short step asymmetric synthesis of 6-substituted 5,6-dehydro-2-pyrones", Tetrahedron (1993) 49(10):1997-2010.
Singh et al., "Asymmetric Homologation of Boronic Esters Bearing Azido and Silyloxy Substituents", J Org Chem. (2000) 65(20):6650-6653 and Erratum: J Org Chem. (2001) 66(22):7560.
Sliwka et al., "Synthetic Sulfur Carotenoids II: Optically Active Carotenoid Thiols", Tetrahedron: Asymmetry (1993) 4(3):361-368.
Solladié et al., "First Stereocontrolled Synthesis of the (3S,5R,7R,10R,11R)-C1-C13 Fragment of Nystatin A(1)", J Org Chem. (1999) 64(15):5447-5452.
Souto et al., "Synthesis and biological characterization of the histone deacetylase inhibitor largazole and c7-modified analogues", J. Med. Chem. (2010) 53(12):4654-4667.
Spiegel et al., "CP-263,114 synthetic studies. Construction of an isotwistane ring system via rhodium carbenoid C—H insertion", Tetrahedron (2002) 58:6545-6554.
Sun et al., "Programmed Synthesis of a Contiguous Stereotriad Motif by Triple Stereospecific Reagent-controlled Homologation", Org Lttr. (Jul. 2013) 15(17):4500-4503.
Teo et al., "Efficient and highly aldehyde selective Wacker oxidation", Org Lett. (2012) 14(13):3237-3239.
Theuretzbacher et al., "Update on antibacterial and antifungal drugs—can we master the resistance crisis?", Curr Opin Pharmacol. (2011) 11:429-432.
Vasil'Ev et al., (1977): STN International HCAPLUS database, Columbus (OH), accession No. 1977: 72730; 1 page.
Vitor et al., "Rhenium(I)- and technetium(I) tricarbonyl complexes anchored by bifunctional pyrazole-diamine and pyrazole-dithioether chelators", J Organometal Chem (2004) 689(25):4764-4774.
Waley, Stephen G., "A quick method for the determination of inhibition constants", Biochem J. (1982) 205(3):631-633.
Walsh et al., "Metallo-beta-Lactamases: the Quiet before the Storm?", Clin Microbiol Rev. (2005) 18(2):306-325.
Wang et al., "Recognition and resistance in TEM beta-lactamase", Biochemistry (2003) 42(28):8434-8444.

(56) References Cited

OTHER PUBLICATIONS

Webb et al., "Metal catalysed hydroboration of vinyl sulfides, sulfoxides, sulfones, and sulfonates", J Mol Cat A: Chem. (2007) 275:91-100.

Wohlrab et al., "Total synthesis of plusbacin A3: a depsipeptide antibiotic active against vancomycin-resistant bacteria", J. Am. Chem. Soc. (2007) 129:4175-4177.

Xia et al., "Synthesis and SAR of novel benzoxaboroles as a new class of beta-lactamase inhibitors", Bioorg Med Chem Lett. (2011) 21:2533-2536.

Xie et al., "Group-assisted purification (GAP) chemistry for the synthesis of Velcade via asymmetric borylation of N-phosphinylimines", Beilstein J Org Chem (Mar. 2014) 10:746-751.

Yamamoto et al., "Iridium-catalyzed hydroboration of alkenes with pinacolborane", Tetrahedron (2004) 60:10695-10700.

Yanagisawa et al., "Nonpeptide angiotensin II receptor antagonists: synthesis, biological activities, and structure-activity relationships of imidazole-5-carboxylic acids bearing alkyl, alkenyl, and hydroxyalkyl substituents at the 4-position and their related compounds", J Med Chem. (1996) 39(1):323-338.

Yuen et al., "Deprotection of pinacolyl boronate esters via hydrolysis of intermediate potassium trifluoroborates", Tetrahed Lttr. (2005)46(46):7899-7903.

International Preliminary Report of Patentability dated Nov. 8, 2016 for International Application No. PCT/US2015/028613, filed Apr. 30, 2015.

SYNTHESIS OF BORONATE SALTS AND USES THEREOF

CROSS-REFERENCE TO RELATED APPLICATIONS

This application is the National Phase Entry of International Application No. PCT/US2015/028613, filed Apr. 30, 2015, published in English as WO2015/171430, which claims the benefit of priority to U.S. Provisional Patent Application No. 61/988,690, filed May 5, 2014; each of the aforementioned applications is hereby expressly incorporated by reference in its entirety. Any and all applications for which a foreign or domestic priority claim is identified in the Application Data Sheet as filed with the present application are hereby incorporated by reference under 37 CFR 1.57.

BACKGROUND OF THE INVENTION

Field of the Invention

The present application relates to certain compounds and to methods for the preparation of certain compounds that can be used in the fields of chemistry and medicine. More specifically, the present application relates to intermediates and methods in the synthesis of boronic acid antimicrobial compounds.

Description of the Related Art

Antibiotics have been effective tools in the treatment of infectious diseases during the last half-century. From the development of antibiotic therapy to the late 1980s there was almost complete control over bacterial infections in developed countries. However, in response to the pressure of antibiotic usage, multiple resistance mechanisms have become widespread and are threatening the clinical utility of anti-bacterial therapy. The increase in antibiotic resistant strains has been particularly common in major hospitals and care centers. The consequences of the increase in resistant strains include higher morbidity and mortality, longer patient hospitalization, and an increase in treatment costs.

Various bacteria have evolved β-lactam deactivating enzymes, namely, β-lactamases, that counter the efficacy of the various β-lactam antibiotics. β-lactamases can be grouped into 4 classes based on their amino acid sequences, namely, Ambler classes A, B, C, and D. Enzymes in classes A, C, and D include active-site serine β-lactamases, and class B enzymes, which are encountered less frequently, are Zn-dependent. These enzymes catalyze the chemical degradation of β-lactam antibiotics, rendering them inactive. Some β-lactamases can be transferred within and between various bacterial strains and species. The rapid spread of bacterial resistance and the evolution of multi-resistant strains severely limits β-lactam treatment options available.

The increase of class D β-lactamase-expressing bacterium strains such as *Acinetobacter baumannii* has become an emerging multidrug-resistant threat. *A. baumannii* strains express A, C, and D class β-lactamases. The class D β-lactamases such as the OXA families are particularly effective at destroying carbapenem type β-lactam antibiotics, e.g., imipenem, the active carbapenems component of Merck's Primaxin® (Montefour, K.; et al. Crit. Care Nurse 2008, 28, 15; Perez, F. et al. Expert Rev. Anti Infect. Ther. 2008, 6, 269; Bou, G.; Martinez-Beltran, J. Antimicrob. Agents Chemother. 2000, 40, 428. 2006, 50, 2280; Bou, G. et al, J. Antimicrob. Agents Chemother. 2000, 44, 1556). This has imposed a pressing threat to the effective use of drugs in that category to treat and prevent bacterial infections. Indeed the number of catalogued serine-based β-lactamases has exploded from less than ten in the 1970s to over 300 variants. These issues fostered the development of five "generations" of cephalosporins. When initially released into clinical practice, extended-spectrum cephalosporins resisted hydrolysis by the prevalent class A β-lactamases, TEM-1 and SHV-1. However, the development of resistant strains by the evolution of single amino acid substitutions in TEM-1 and SHV-1 resulted in the emergence of the extended-spectrum β-lactamase (ESBL) phenotype.

New β-lactamases have recently evolved that hydrolyze the carbapenem class of antimicrobials, including imipenem, biapenem, doripenem, meropenem, and ertapenem, as well as other β-lactam antibiotics. These carbapenemases belong to molecular classes A, B, and D. Class A carbapenemases of the KPC-type predominantly in *Klebsiella pneumoniae* but now also reported in other Enterobacteriaceae, *Pseudomonas aeruginosa* and *Acinetobacter baumannii*. The KPC carbapenemase was first described in 1996 in North Carolina, but since then has disseminated widely in the US. It has been particularly problematic in the New York City area, where several reports of spread within major hospitals and patient morbidity have been reported. These enzymes have also been recently reported in France, Greece, Sweden, United Kingdom, and an outbreak in Germany has recently been reported. Treatment of resistant strains with carbapenems can be associated with poor outcomes.

Another mechanism of β-lactamase mediated resistance to carbapenems involves combination of permeability or efflux mechanisms combined with hyper production of beta-lactamases. One example is the loss of a porin combined in hyperproduction of ampC beta-lactamase results in resistance to imipenem in *Pseudomonas aeruginosa*. Efflux pump over expression combined with hyperproduction of the ampC β-lactamase can also result in resistance to a carbapenem such as meropenem.

Thus, there is a need for improved β-lactamase inhibitors and efficient methods for making these improved β-lactamase inhibitors.

SUMMARY OF THE INVENTION

Some embodiments of the present application provide a compound of Formula (I) or a salt thereof:

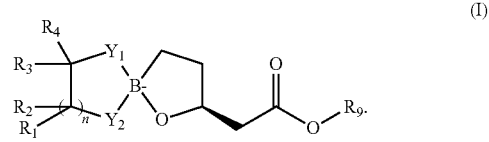

(I)

In some embodiments, n is 0 or 1.

In some embodiments, $Y_1$ is O or $N^+R_5R_6$.

In some embodiments, $Y_2$ is O or $NR_{10}$.

In some embodiments, $R_1$ and $R_2$ are independently selected from the group consisting of H, optionally substituted phenyl and optionally substituted $C_{1-4}$ alkyl, or $R_1$ and $R_2$ together with the atoms to which they are attached, form =O.

In some embodiments, $R_3$ is selected from the group consisting of H, optionally substituted phenyl and optionally substituted $C_{1-4}$ alkyl, or $R_3$ and $R_5$, together with the atoms to which they are attached, form a heteroaryl ring; or $R_3$ and $R_4$ together with the atoms to which they are attached, form =O.

In some embodiments, $R_4$, $R_5$, $R_6$, and $R_{10}$ are independently selected from the group consisting of H, optionally substituted phenyl and optionally substituted $C_{1-4}$ alkyl.

In some embodiments, $R_9$ is selected from the group consisting of optionally substituted $C_1$-$C_{12}$ alkyl, optionally substituted $C_3$-$C_8$ cycloalkyl, optionally substituted $C_2$-$C_{12}$ alkenyl, optionally substituted $C_2$-$C_{12}$ alkynyl, optionally substituted aryl and optionally substituted heteroaryl.

In some embodiments, $R_1$ is H. In some embodiments, $R_1$ is optionally substituted phenyl. In some embodiments, $R_1$ is optionally substituted $C_{1-4}$ alkyl.

In some embodiments, $R_2$ is H. In some embodiments, $R_2$ is optionally substituted phenyl. In some embodiments, $R_2$ is optionally substituted $C_{1-4}$ alkyl.

In some embodiments, $R_1$ and $R_2$ together with the atoms to which they are attached, form =O. In some embodiments, $R_3$ and $R_4$ together with the atoms to which they are attached, form =O. In some embodiments, $R_1$ and $R_2$ together with the atoms to which they are attached, form =O and wherein $R_3$ and $R_4$ together with the atoms to which they are attached, form =O.

In some embodiments, $R_3$ is H. In some embodiments, $R_3$ is optionally substituted phenyl. In some embodiments, $R_3$ is $C_{1-4}$ optionally substituted alkyl. In some embodiments, $R_1$ and $R_3$ together with the atoms to which they are attached form carbocyclic ring. In some embodiments, $R_3$ and $R_5$, together with the atoms to which they are attached, form a heteroaryl ring.

In some embodiments, $R_4$ is H. In some embodiments, $R_4$ is optionally substituted phenyl. In some embodiments, $R_4$ is optionally substituted $C_{1-4}$ alkyl.

In some embodiments, $R_5$ is H. In some embodiments, $R_5$ is optionally substituted phenyl. In some embodiments, $R_5$ is optionally substituted $C_{1-4}$ alkyl.

In some embodiments, $R_6$ is H. In some embodiments, $R_6$ is optionally substituted phenyl. In some embodiments, $R_6$ is optionally substituted $C_{1-4}$ alkyl.

In some embodiments, $R_{10}$ is H. In some embodiments, $R_{10}$ is optionally substituted phenyl. In some embodiments, $R_{10}$ is optionally substituted $C_{1-4}$ alkyl.

In some embodiments, $R_9$ is optionally substituted $C_1$-$C_{12}$ alkyl. In some embodiments, $R_9$ is t-butyl. In some embodiments, $R_9$ is optionally substituted $C_3$-$C_8$ cycloalkyl. In some embodiments, $R_9$ is optionally substituted $C_2$-$C_{12}$ alkenyl. In some embodiments, $R_9$ is optionally substituted $C_2$-$C_{12}$ alkynyl. In some embodiments, $R_9$ is optionally substituted aryl. In some embodiments, $R_9$ is optionally substituted heteroaryl.

In some embodiments, each $C_{1-4}$ alkyl is optionally substituted with one or more substituents independently selected from the group consisting of OMe, and phenyl. In some embodiments, each $C_{1-4}$ alkyl is optionally substituted with OMe. In some embodiments, each $C_{1-4}$ alkyl is optionally substituted with phenyl. In some embodiments, each phenyl is optionally substituted with one to three substitutions independently selected from the group consisting of OMe, and halogen. In some embodiments, each phenyl is optionally substituted with OMe. In some embodiments, each phenyl is optionally substituted with halogen.

In some embodiments, the compound of Formula (I) is selected from the group consisting of:

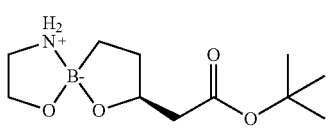

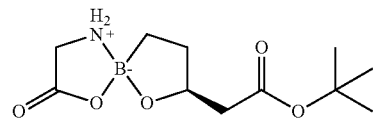

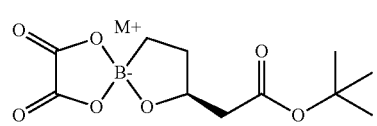

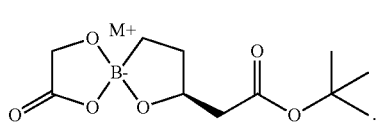

In some embodiments, $M^+$ is a cation selected from the group consisting of lithium, sodium, potassium, calcium, ammonium, triethylammonium, and aluminum.

Some embodiments of the present application provides a method of making a compound of Formula (I), or a salt thereof:

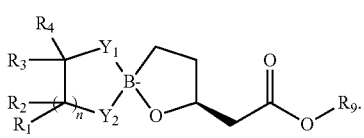

(I)

In some embodiments, the method of making comprises the steps of: protecting the primary hydroxy group of the compound of Formula (A)

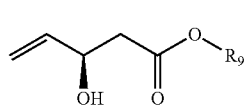

(A)

to form a compound of Formula (B):

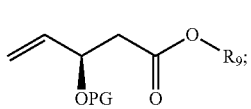

(B)

reacting a compound of Formula (B) with a compound of Formula (C):

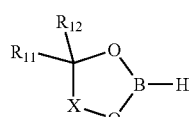

(C)

to form a compound of Formula (D):

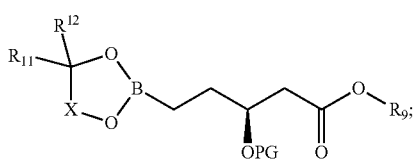

deprotecting a compound of Formula (D) to form a compound of Formula (E):

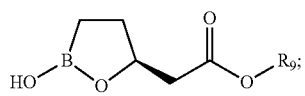

reacting a compound of Formula (E) with a complexing agent of Formula (F):

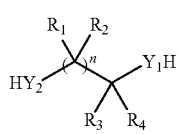

to form a compound of Formula (I):

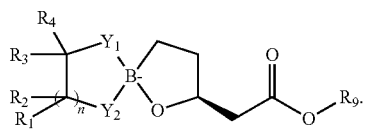

In some embodiments, n is 0 or 1.

In some embodiments, $Y_1$ is O or $N^+R_5R_6$.

In some embodiments, $Y_2$ is O or $NR_{10}$.

In some embodiments, $R_1$ and $R_2$ are independently selected from the group consisting of H, optionally substituted phenyl and optionally substituted $C_{1-4}$ alkyl, or $R_1$ and $R_2$ together with the atoms to which they are attached, form =O.

In some embodiments, $R_3$ is selected from the group consisting of H, optionally substituted phenyl and optionally substituted $C_{1-4}$ alkyl, or $R_3$ and $R_5$, together with the atoms to which they are attached, form a heteroaryl ring; or $R_3$ and $R_4$ together with the atoms to which they are attached, form =O.

In some embodiments, $R_4$, $R_5$, $R_6$, and $R_{10}$ are independently selected from the group consisting of H, optionally substituted phenyl and optionally substituted $C_{1-4}$ alkyl.

In some embodiments, $R_9$ is selected from the group consisting of optionally substituted $C_1-C_{12}$ alkyl, optionally substituted $C_3-C_8$ cycloalkyl, optionally substituted $C_2-C_{12}$ alkenyl, optionally substituted $C_2-C_{12}$ alkynyl, optionally substituted aryl and optionally substituted heteroaryl.

In some embodiments, $R_1$ is H. In some embodiments, $R_1$ is optionally substituted phenyl. In some embodiments, $R_1$ is optionally substituted $C_{1-4}$ alkyl.

In some embodiments, $R_2$ is H. In some embodiments, $R_2$ is optionally substituted phenyl. In some embodiments, $R_2$ is optionally substituted $C_{1-4}$ alkyl.

In some embodiments, $R_1$ and $R_2$ together with the atoms to which they are attached, form =O. In some embodiments, $R_3$ and $R_4$ together with the atoms to which they are attached, form =O. In some embodiments, $R_1$ and $R_2$ together with the atoms to which they are attached, form =O and wherein $R_3$ and $R_4$ together with the atoms to which they are attached, form =O.

In some embodiments, $R_3$ is H. In some embodiments, $R_3$ is optionally substituted phenyl. In some embodiments, $R_3$ is $C_{1-4}$ optionally substituted alkyl. In some embodiments, $R_1$ and $R_3$ together with the atoms to which they are attached form carbocyclic ring. In some embodiments, $R_3$ and $R_5$, together with the atoms to which they are attached, form a heteroaryl ring.

In some embodiments, $R_4$ is H. In some embodiments, $R_4$ is optionally substituted phenyl. In some embodiments, $R_4$ is optionally substituted $C_{1-4}$ alkyl.

In some embodiments, $R_5$ is H. In some embodiments, $R_5$ is optionally substituted phenyl. In some embodiments, $R_5$ is optionally substituted $C_{1-4}$ alkyl.

In some embodiments, $R_6$ is H. In some embodiments, $R_6$ is optionally substituted phenyl. In some embodiments, $R_6$ is optionally substituted $C_{1-4}$ alkyl.

In some embodiments, $R_{10}$ is H. In some embodiments, $R_{10}$ is optionally substituted phenyl. In some embodiments, $R_{10}$ is optionally substituted $C_{1-4}$ alkyl.

In some embodiments, $R_9$ is optionally substituted $C_1-C_{12}$ alkyl. In some embodiments, $R_9$ is t-butyl. In some embodiments, $R_9$ is optionally substituted $C_3-C_8$ cycloalkyl. In some embodiments, $R_9$ is optionally substituted $C_2-C_{12}$ alkenyl. In some embodiments, $R_9$ is optionally substituted $C_2-C_{12}$ alkynyl. In some embodiments, $R_9$ is optionally substituted aryl. In some embodiments, $R_9$ is optionally substituted heteroaryl.

In some embodiments, each $C_{1-4}$ alkyl is optionally substituted with one or more substituents independently selected from the group consisting of OMe, and phenyl. In some embodiments, each $C_{1-4}$ alkyl is optionally substituted with OMe. In some embodiments, each $C_{1-4}$ alkyl is optionally substituted with phenyl. In some embodiments, each phenyl is optionally substituted with one to three substitutions independently selected from the group consisting of OMe, and halogen. In some embodiments, each phenyl is optionally substituted with OMe. In some embodiments, each phenyl is optionally substituted with halogen.

In some embodiments, the compound of Formula (I) is selected from the group consisting of:

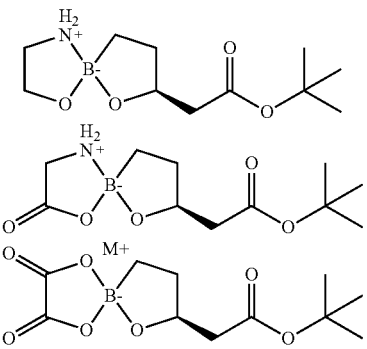

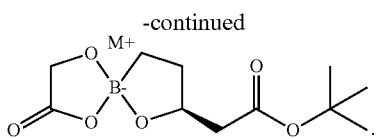

In some embodiments, $M^+$ is a cation selected from the group consisting of lithium, sodium, potassium, calcium, ammonium, triethylammonium, and aluminum.

In some embodiments, PG is a hydroxyl protecting group. In some embodiments, PG is a trialkylsilyl group. In some embodiments, PG is trimethylsilyl.

In some embodiments, $R_{11}$ is selected from the group consisting of substituted or unsubstituted variants of the following: $C_1$-$C_{12}$ alkyl, $C_2$-$C_{12}$ alkenyl, $C_2$-$C_{12}$ alkynyl, $C_3$-$C_{12}$ cycloalkyl, $C_3$-$C_{12}$ cycloalkenyl, $C_3$-$C_{12}$ cycloalkynyl, $C_3$-$C_{12}$ heterocyclyl, aryl, heteroaryl, arylalkyl, heteroarylalkyl, and (cycloalkyl)alkyl.

In some embodiments, X is selected from the group consisting of substituted or unsubstituted variants of the following: $C_1$-$C_1$ alkyl, $C_2$-$C_4$ alkenyl, and $C_2$-$C_4$ alkynyl.

In some embodiments, $R_{12}$ is selected from the group consisting of substituted or unsubstituted variants of the following: $C_1$-$C_{12}$ alkyl, $C_2$-$C_{12}$ alkenyl, $C_2$-$C_{12}$ alkynyl, $C_3$-$C_{12}$ cycloalkyl, $C_3$-$C_{12}$ cycloalkenyl, $C_3$-$C_{12}$ cycloalkynyl, $C_3$-$C_{12}$ heterocyclyl, aryl, heteroaryl, arylalkyl, heteroarylalkyl, and (cycloalkyl)alkyl.

In some embodiments, $R_{11}$ is optionally substituted $C_1$-$C_{12}$ alkyl. In some embodiments, $R_{11}$ is optionally substituted $C_2$-$C_{12}$ alkenyl. In some embodiments, $R_{11}$ is optionally substituted $C_2$-$C_{12}$ alkynyl. In some embodiments, $R_{11}$ is optionally substituted $C_3$-$C_{12}$ cycloalkyl. In some embodiments, $R_{11}$ is optionally substituted $C_3$-$C_{12}$ cycloalkenyl. In some embodiments, $R_{11}$ is optionally substituted $C_3$-$C_{12}$ cycloalkynyl. In some embodiments, $R_{11}$ is optionally substituted $C_3$-$C_{12}$ heterocyclyl. In some embodiments, $R_{11}$ is optionally substituted aryl. In some embodiments, $R_{11}$ is optionally substituted heteroaryl. In some embodiments, $R_{11}$ is optionally substituted arylalkyl. In some embodiments, $R_{11}$ is optionally substituted heteroarylalkyl. In some embodiments, $R_{11}$ is optionally substituted (cycloalkyl)alkyl.

In some embodiments, X is optionally substituted $C_1$-$C_4$ alkyl. In some embodiments, X is optionally substituted $C_2$-$C_4$ alkenyl. In some embodiments, X is optionally substituted $C_2$-$C_4$ alkynyl.

In some embodiments, $R_{12}$ is optionally substituted $C_1$-$C_{12}$ alkyl. In some embodiments, $R_{12}$ is optionally substituted $C_2$-$C_{12}$ alkenyl. In some embodiments, $R_{12}$ is optionally substituted $C_2$-$C_{12}$ alkynyl. In some embodiments, $R_{12}$ is optionally substituted $C_3$-$C_{12}$ cycloalkyl. In some embodiments, $R_{12}$ is optionally substituted $C_3$-$C_{12}$ cycloalkenyl. In some embodiments, $R_{12}$ is optionally substituted $C_3$-$C_{12}$ cycloalkynyl. In some embodiments, $R_{12}$ is optionally substituted $C_3$-$C_{12}$ heterocyclyl. In some embodiments, $R_{12}$ is optionally substituted aryl. In some embodiments, $R_{12}$ is optionally substituted heteroaryl. In some embodiments, $R_{12}$ is optionally substituted arylalkyl. In some embodiments, $R_{12}$ is optionally substituted heteroarylalkyl. In some embodiments, $R_{12}$ is optionally substituted (cycloalkyl)alkyl.

In some embodiments, each $C_{1-4}$ alkyl is optionally substituted with one or more substituents independently selected from the group consisting of OMe, and phenyl. In some embodiments, each $C_{1-4}$ alkyl is optionally substituted with OMe. In some embodiments, each $C_{1-4}$ alkyl is optionally substituted with phenyl. In some embodiments, each phenyl is optionally substituted with one to three substitutions independently selected from the group consisting of OMe, and halogen. In some embodiments, each phenyl is optionally substituted with OMe. In some embodiments, each phenyl is optionally substituted with halogen.

Some embodiments of the present application provides a method of making a compound of Formula (D):

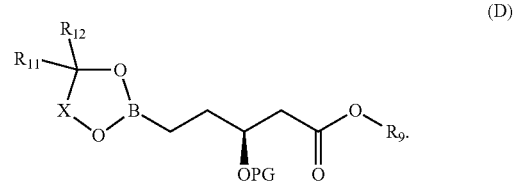

In some embodiments, the method of making comprises the steps of: reacting a compound of Formula (B):

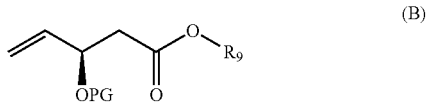

with a compound of Formula (C):

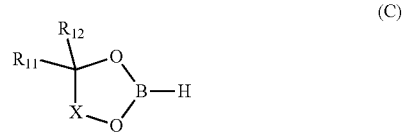

to form a compound of Formula (D):

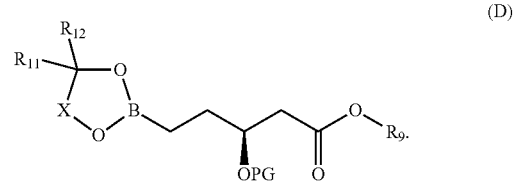

In some embodiments, $R_9$ is optionally substituted $C_1$-$C_{12}$ alkyl. In some embodiments, $R_9$ is t-butyl. In some embodiments, $R_9$ is optionally substituted $C_3$-$C_8$ cycloalkyl. In some embodiments, $R_9$ is optionally substituted $C_2$-$C_{12}$ alkenyl. In some embodiments, $R_9$ is optionally substituted $C_2$-$C_{12}$ alkynyl. In some embodiments, $R_9$ is optionally substituted aryl. In some embodiments, $R_9$ is optionally substituted heteroaryl.

In some embodiments, $R_{11}$ is selected from the group consisting of substituted or unsubstituted variants of the following: $C_1$-$C_{12}$ alkyl, $C_2$-$C_{12}$ alkenyl, $C_2$-$C_{12}$ alkynyl, $C_3$-$C_{12}$ cycloalkyl, $C_3$-$C_{12}$ cycloalkenyl, $C_3$-$C_{12}$ cycloalkynyl, $C_3$-$C_{12}$ heterocyclyl, aryl, heteroaryl, arylalkyl, heteroarylalkyl, and (cycloalkyl)alkyl.

In some embodiments, X is selected from the group consisting of substituted or unsubstituted variants of the following: $C_1$-$C_4$ alkyl, $C_2$-$C_4$ alkenyl, and $C_2$-$C_4$ alkynyl.

In some embodiments, $R_{12}$ is selected from the group consisting of substituted or unsubstituted variants of the following: $C_1$-$C_{12}$ alkyl, $C_2$-$C_{12}$ alkenyl, $C_2$-$C_{12}$ alkynyl, $C_3$-$C_{12}$ cycloalkyl, $C_3$-$C_{12}$ cycloalkenyl, $C_3$-$C_{12}$ cycloalkynyl, $C_3$-$C_{12}$ heterocyclyl, aryl, heteroaryl, arylalkyl, heteroarylalkyl, and (cycloalkyl)alkyl.

In some embodiments, $R_{11}$ is optionally substituted $C_1$-$C_{12}$ alkyl. In some embodiments, $R_{11}$ is optionally substituted $C_2$-$C_{12}$ alkenyl. In some embodiments, $R_{11}$ is optionally substituted $C_2$-$C_{12}$ alkynyl. In some embodiments, $R_{11}$ is optionally substituted $C_3$-$C_{12}$ cycloalkyl. In some embodiments, $R_{11}$ is optionally substituted $C_3$-$C_{12}$ cycloalkenyl. In some embodiments, $R_{11}$ is optionally substituted $C_3$-$C_{12}$ cycloalkynyl. In some embodiments, $R_{11}$ is optionally substituted $C_3$-$C_{12}$ heterocyclyl. In some embodiments, $R_{11}$ is optionally substituted aryl. In some embodiments, $R_{11}$ is optionally substituted heteroaryl. In some embodiments, $R_{11}$ is optionally substituted arylalkyl. In some embodiments, $R_{11}$ is optionally substituted heteroarylalkyl. In some embodiments, $R_{11}$ is optionally substituted (cycloalkyl)alkyl.

In some embodiments, X is optionally substituted $C_1$-$C_4$ alkyl. In some embodiments, X is optionally substituted $C_2$-$C_4$ alkenyl. In some embodiments, X is optionally substituted $C_2$-$C_4$ alkynyl.

In some embodiments, $R_{12}$ is optionally substituted $C_1$-$C_{12}$ alkyl. In some embodiments, $R_{12}$ is optionally substituted $C_2$-$C_{12}$ alkenyl. In some embodiments, $R_{12}$ is optionally substituted $C_2$-$C_{12}$ alkynyl. In some embodiments, $R_{12}$ is optionally substituted $C_3$-$C_{12}$ cycloalkyl. In some embodiments, $R_{12}$ is optionally substituted $C_3$-$C_{12}$ cycloalkenyl. In some embodiments, $R_{12}$ is optionally substituted $C_3$-$C_{12}$ cycloalkynyl. In some embodiments, $R_{12}$ is optionally substituted $C_3$-$C_{12}$ heterocyclyl. In some embodiments, $R_{12}$ is optionally substituted aryl. In some embodiments, $R_{12}$ is optionally substituted heteroaryl. In some embodiments, $R_{12}$ is optionally substituted arylalkyl. In some embodiments, $R_{12}$ is optionally substituted heteroarylalkyl. In some embodiments, $R_{12}$ is optionally substituted (cycloalkyl)alkyl.

In some embodiments, each $C_{1-4}$ alkyl is optionally substituted with one or more substituents independently selected from the group consisting of OMe, and phenyl. In some embodiments, each $C_{1-4}$ alkyl is optionally substituted with OMe. In some embodiments, each $C_{1-4}$ alkyl is optionally substituted with phenyl. In some embodiments, each phenyl is optionally substituted with one to three substitutions independently selected from the group consisting of OMe, and halogen. In some embodiments, each phenyl is optionally substituted with OMe. In some embodiments, each phenyl is optionally substituted with halogen.

In some embodiments, PG is a hydroxyl protecting group. In some embodiments, PG is a trialkylsilyl group. In some embodiments, PG is trimethylsilyl.

Some embodiments of the present application provides a method of making a compound of Formula (I), or a salt thereof:

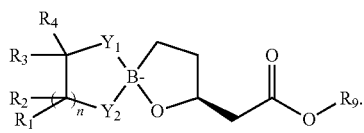

In some embodiments, the method of making comprises the steps of: reacting a compound of Formula (E):

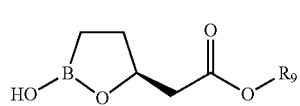

(E)

with a complexing agent of Formula (F):

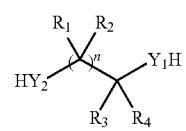

(F)

to form a compound of Formula (I):

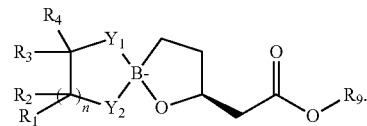

In some embodiments, n is 0 or 1.
In some embodiments, $Y_1$ is O or $N^+R_5R_6$.
In some embodiments, $Y_2$=O or $NR_{10}$.
In some embodiments, $R_1$, $R_2$, $R_3$, $R_4$, $R_5$, $R_6$, and $R_{10}$ are independently selected from the group consisting of H, optionally substituted phenyl and optionally substituted $C_{1-4}$ alkyl.

In some embodiments, independently two germinal $R_1$, $R_2$, $R_3$, $R_4$ together with the atoms to which they are attached, form =O.

In some embodiments, $R_9$ is optionally substituted $C_1$-$C_{12}$ alkyl, optionally substituted $C_3$-$C_8$ cycloalkyl, optionally substituted $C_2$-$C_{12}$ alkenyl, optionally substituted $C_2$-$C_{12}$ alkynyl, optionally substituted aryl or optionally substituted heteroaryl.

In some embodiments, $R_1$ is H. In some embodiments, $R_1$ is optionally substituted phenyl. In some embodiments, $R_1$ is optionally substituted $C_{1-4}$ alkyl.

In some embodiments, $R_2$ is H. In some embodiments, $R_2$ is optionally substituted phenyl. In some embodiments, $R_2$ is optionally substituted $C_{1-4}$ alkyl.

In some embodiments, $R_1$ and $R_2$ together with the atoms to which they are attached, form =O.

In some embodiments, $R_3$ is H. In some embodiments, $R_3$ is optionally substituted phenyl. In some embodiments, $R_3$ is optionally substituted $C_{1-4}$ alkyl.

In some embodiments, $R_4$ is H. In some embodiments, $R_4$ is optionally substituted phenyl. In some embodiments, $R_4$ is optionally substituted $C_{1-4}$ alkyl.

In some embodiments, $R_3$ and $R_4$ together with the atoms to which they are attached, form =O. In some embodiments, $R_1$ and $R_2$ together with the atoms to which they are attached, form =O and wherein $R_3$ and $R_4$ together with the atoms to which they are attached, form =O.

In some embodiments, $R_5$ is H. In some embodiments, $R_5$ is optionally substituted phenyl. In some embodiments, $R_5$ is optionally substituted $C_{1-4}$ alkyl.

In some embodiments, $R_6$ is H. In some embodiments, $R_6$ is optionally substituted phenyl. In some embodiments, $R_6$ is optionally substituted $C_{1-4}$ alkyl.

In some embodiments, $R_{10}$ is H. In some embodiments, $R_{10}$ is optionally substituted phenyl. In some embodiments, $R_{10}$ is optionally substituted $C_{1-4}$ alkyl.

In some embodiments, $R_9$ is optionally substituted $C_1$-$C_{12}$ alkyl. In some embodiments, $R_9$ is t-butyl. In some embodiments, $R_9$ is optionally substituted $C_3$-$C_8$ cycloalkyl. In some embodiments, $R_9$ is optionally substituted $C_2$-$C_{12}$ alkenyl. In some embodiments, $R_9$ is optionally substituted $C_2$-$C_{12}$ alkynyl. In some embodiments, $R_9$ is optionally substituted aryl. In some embodiments, $R_9$ is optionally substituted heteroaryl.

In some embodiments, each $C_{1-4}$ alkyl is optionally substituted with one or more substituents independently selected from the group consisting of OMe, and phenyl. In some embodiments, each $C_{1-4}$ alkyl is optionally substituted with OMe. In some embodiments, each $C_{1-4}$ alkyl is optionally substituted with phenyl. In some embodiments, each phenyl is optionally substituted with one to three substitutions independently selected from the group consisting of OMe, and halogen. In some embodiments, each phenyl is optionally substituted with OMe. In some embodiments, each phenyl is optionally substituted with halogen.

DETAILED DESCRIPTION OF THE PREFERRED EMBODIMENT

Numerous references are cited herein. The references cited herein, including the U.S. patents cited herein, are each to be considered incorporated by reference in their entirety into this specification.

Embodiments of the invention include, but are not limited to, methods for the preparation of various compounds and intermediates, and the compounds and intermediates themselves. In some embodiments, one or more substituents, one or more compounds, or groups of compounds can be specifically excluded in any one or more of the methods or compounds as described more fully below.

Where the compounds disclosed herein have at least one chiral center, they may exist as individual enantiomers and diastereomers or as mixtures of such isomers, including racemates. Separation of the individual isomers or selective synthesis of the individual isomers is accomplished by application of various methods which are well known to practitioners in the art. Unless otherwise indicated, all such isomers and mixtures thereof are included in the scope of the compounds disclosed herein. Furthermore, compounds disclosed herein may exist in one or more crystalline or amorphous forms. Unless otherwise indicated, all such forms are included in the scope of the compounds disclosed herein including any polymorphic forms. In addition, some of the compounds disclosed herein may form solvates with water (i.e., hydrates) or common organic solvents. Unless otherwise indicated, such solvates are included in the scope of the compounds disclosed herein. Additionally, in some embodiments, the compounds disclosed herein can form oligomers and other higher-order polymers.

The skilled artisan will recognize that some structures described herein may be resonance forms or tautomers of compounds that may be fairly represented by other chemical structures, even when kinetically; the artisan recognizes that such structures may only represent a very small portion of a sample of such compound(s). Such compounds are considered within the scope of the structures depicted, though such resonance forms or tautomers are not represented herein.

Isotopes may be present in the compounds described. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

Definitions

"Solvate" refers to the compound formed by the interaction of a solvent and a compound described herein or salt thereof. Suitable solvates are pharmaceutically acceptable solvates including hydrates.

The term "pharmaceutically acceptable salt" refers to salts that retain the biological effectiveness and properties of a compound and, which are not biologically or otherwise undesirable for use in a pharmaceutical. In many cases, the compounds disclosed herein are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. Many such salts are known in the art, as described in WO 87/05297, Johnston et al., published Sep. 11, 1987 (incorporated by reference herein in its entirety).

As used herein, "$C_a$ to $C_b$" or "$C_{a-b}$" in which "a" and "b" are integers refer to the number of carbon atoms in the specified group. That is, the group can contain from "a" to "b", inclusive, carbon atoms. Thus, for example, a "$C_1$ to $C_4$ alkyl" or "$C_{1-4}$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—.

The term "halogen" or "halo," as used herein, means any one of the radio-stable atoms of column 7 of the Periodic Table of the Elements, e.g., fluorine, chlorine, bromine, or iodine, with fluorine and chlorine being preferred.

As used herein, "alkyl" refers to a straight or branched hydrocarbon chain that is fully saturated (i.e., contains no double or triple bonds). The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 9 carbon atoms. The alkyl group could also be a lower alkyl having 1 to 4 carbon atoms. The alkyl group may be designated as "$C_{1-4}$ alkyl" or similar designations. By way of example only, "$C_{1-4}$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like.

As used herein, "alkoxy" refers to the formula —OR wherein R is an alkyl as is defined above, such as "$C_{1-9}$ alkoxy", including but not limited to methoxy, ethoxy, n-propoxy, 1-methylethoxy (isopropoxy), n-butoxy, iso-butoxy, sec-butoxy, and tert-butoxy, and the like.

As used herein, "alkylthio" refers to the formula —SR wherein R is an alkyl as is defined above, such as "$C_{1-9}$ alkylthio" and the like, including but not limited to methylmercapto, ethylmercapto, n-propylmercapto, 1-methylethylmercapto (isopropylmercapto), n-butylmercapto, iso-butylmercapto, sec-butylmercapto, tert-butylmercapto, and the like.

As used herein, "alkenyl" refers to a straight or branched hydrocarbon chain containing one or more double bonds. The alkenyl group may have 2 to 20 carbon atoms, although the present definition also covers the occurrence of the term "alkenyl" where no numerical range is designated. The alkenyl group may also be a medium size alkenyl having 2 to 9 carbon atoms. The alkenyl group could also be a lower alkenyl having 2 to 4 carbon atoms. The alkenyl group may be designated as "$C_{2-4}$ alkenyl" or similar designations. By way of example only, "$C_{2-4}$ alkenyl" indicates that there are two to four carbon atoms in the alkenyl chain, i.e., the alkenyl chain is selected from the group consisting of ethenyl, propen-1-yl, propen-2-yl, propen-3-yl, buten-1-yl, buten-2-yl, buten-3-yl, buten-4-yl, 1-methyl-propen-1-yl, 2-methyl-propen-1-yl, 1-ethyl-ethen-1-yl, 2-methyl-propen-3-yl, buta-1,3-dienyl, buta-1,2,-dienyl, and buta-1,2-dien-4-yl. Typical alkenyl groups include, but are in no way limited to, ethenyl, propenyl, butenyl, pentenyl, and hexenyl, and the like.

As used herein, "alkynyl" refers to a straight or branched hydrocarbon chain containing one or more triple bonds. The alkynyl group may have 2 to 20 carbon atoms, although the present definition also covers the occurrence of the term "alkynyl" where no numerical range is designated. The alkynyl group may also be a medium size alkynyl having 2 to 9 carbon atoms. The alkynyl group could also be a lower alkynyl having 2 to 4 carbon atoms. The alkynyl group may be designated as "$C_{2-4}$ alkynyl" or similar designations. By way of example only, "$C_{2-4}$ alkynyl" indicates that there are two to four carbon atoms in the alkynyl chain, i.e., the alkynyl chain is selected from the group consisting of ethynyl, propyn-1-yl, propyn-2-yl, butyn-1-yl, butyn-3-yl, butyn-4-yl, and 2-butynyl. Typical alkynyl groups include, but are in no way limited to, ethynyl, propynyl, butynyl, pentynyl, and hexynyl, and the like.

As used herein, "heteroalkyl" refers to a straight or branched hydrocarbon chain containing one or more heteroatoms, that is, an element other than carbon, including but not limited to, nitrogen, oxygen and sulfur, in the chain backbone. The heteroalkyl group may have 1 to 20 carbon atom, although the present definition also covers the occurrence of the term "heteroalkyl" where no numerical range is designated. The heteroalkyl group may also be a medium size heteroalkyl having 1 to 9 carbon atoms. The heteroalkyl group could also be a lower heteroalkyl having 1 to 4 carbon atoms. The heteroalkyl group may be designated as "$C_{1-4}$ heteroalkyl" or similar designations. The heteroalkyl group may contain one or more heteroatoms. By way of example only, "$C_{1-4}$ heteroalkyl" indicates that there are one to four carbon atoms in the heteroalkyl chain and additionally one or more heteroatoms in the backbone of the chain.

As used herein, "alkylene" means a branched, or straight chain fully saturated di-radical chemical group containing only carbon and hydrogen that is attached to the rest of the molecule via two points of attachment (i.e., an alkanediyl). The alkylene group may have 1 to 20 carbon atoms, although the present definition also covers the occurrence of the term alkylene where no numerical range is designated. The alkylene group may also be a medium size alkylene having 1 to 9 carbon atoms. The alkylene group could also be a lower alkylene having 1 to 4 carbon atoms. The alkylene group may be designated as "$C_{1-4}$ alkylene" or similar designations. By way of example only, "$C_{1-4}$ alkylene" indicates that there are one to four carbon atoms in the alkylene chain, i.e., the alkylene chain is selected from the group consisting of methylene, ethylene, ethan-1,1-diyl, propylene, propan-1,1-diyl, propan-2,2-diyl, 1-methyl-ethylene, butylene, butan-1,1-diyl, butan-2,2-diyl, 2-methyl-propan-1,1-diyl, 1-methyl-propylene, 2-methyl-propylene, 1,1-dimethyl-ethylene, 1,2-dimethyl-ethylene, and 1-ethyl-ethylene.

As used herein, "alkenylene" means a straight or branched chain di-radical chemical group containing only carbon and hydrogen and containing at least one carbon-carbon double bond that is attached to the rest of the molecule via two points of attachment. The alkenylene group may have 2 to 20 carbon atoms, although the present definition also covers the occurrence of the term alkenylene where no numerical range is designated. The alkenylene group may also be a medium size alkenylene having 2 to 9 carbon atoms. The alkenylene group could also be a lower alkenylene having 2 to 4 carbon atoms. The alkenylene group may be designated as "$C_{2-4}$ alkenylene" or similar designations. By way of example only, "$C_{2-4}$ alkenylene" indicates that there are two to four carbon atoms in the alkenylene chain, i.e., the alkenylene chain is selected from the group consisting of ethenylene, ethen-1,1-diyl, propenylene, propen-1,1-diyl, prop-2-en-1,1-diyl, 1-methyl-ethenylene, but-1-enylene, but-2-enylene, but-1,3-dienylene, buten-1,1-diyl, but-1,3-dien-1,1-diyl, but-2-en-1,1-diyl, but-3-en-1,1-diyl, 1-methyl-prop-2-en-1,1-diyl, 2-methyl-prop-2-en-1,1-diyl, 1-ethyl-ethenylene, 1,2-dimethyl-ethenylene, 1-methyl-propenylene, 2-methyl-propenylene, 3-methyl-propenylene, 2-methyl-propen-1,1-diyl, and 2,2-dimethyl-ethen-1,1-diyl.

The term "aromatic" refers to a ring or ring system having a conjugated pi electron system and includes both carbocyclic aromatic (e.g., phenyl) and heterocyclic aromatic groups (e.g., pyridine). The term includes monocyclic or fused-ring polycyclic (i.e., rings which share adjacent pairs of atoms) groups provided that the entire ring system is aromatic.

As used herein, "aryl" refers to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms, although the present definition also covers the occurrence of the term "aryl" where no numerical range is designated. In some embodiments, the aryl group has 6 to 10 carbon atoms. The aryl group may be designated as "$C_{6-10}$ aryl," "$C_6$ or $C_{10}$ aryl," or similar designations. Examples of aryl groups include, but are not limited to, phenyl, naphthyl, azulenyl, and anthracenyl.

As used herein, "aryloxy" and "arylthio" refers to RO— and RS—, in which R is an aryl as is defined above, such as "$C_{6-10}$ aryloxy" or "$C_{6-10}$ arylthio" and the like, including but not limited to phenyloxy.

An "aralkyl" or "arylalkyl" is an aryl group connected, as a substituent, via an alkylene group, such as "$C_{7-14}$ aralkyl" and the like, including but not limited to benzyl, 2-phenylethyl, 3-phenylpropyl, and naphthylalkyl. In some cases, the alkylene group is a lower alkylene group (i.e., a $C_{1-4}$ alkylene group).

As used herein, "heteroaryl" refers to an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members (i.e., the number of atoms making up the ring backbone, including carbon atoms and heteroatoms), although the present definition also covers the occurrence of the term "heteroaryl" where no numerical range is designated. In some embodiments, the heteroaryl group has 5 to 10 ring members or 5 to 7 ring members. The heteroaryl group may be designated as "5-7 membered heteroaryl," "5-10 membered heteroaryl," or similar designations. Examples of heteroaryl rings include, but are not limited to, furyl, thienyl, phthalazinyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, triazinyl, quinolinyl, isoquinlinyl, benzimidazolyl, benzoxazolyl, benzothiazolyl, indolyl, isoindolyl, and benzothienyl.

A "heteroaralkyl" or "heteroarylalkyl" is heteroaryl group connected, as a substituent, via an alkylene group. Examples include but are not limited to 2-thienylmethyl, 3-thienylmethyl, furylmethyl, thienylethyl, pyrrolylalkyl, pyridylalkyl, isoxazollylalkyl, and imidazolylalkyl. In some cases, the alkylene group is a lower alkylene group (i.e., a $C_{1-4}$ alkylene group).

As used herein, "carbocyclyl" means a non-aromatic cyclic ring or ring system containing only carbon atoms in the ring system backbone. When the carbocyclyl is a ring system, two or more rings may be joined together in a fused, bridged or spiro-connected fashion. Carbocyclyls may have any degree of saturation provided that at least one ring in a ring system is not aromatic. Thus, carbocyclyls include cycloalkyls, cycloalkenyls, and cycloalkynyls. The carbocyclyl group may have 3 to 20 carbon atoms, although the present definition also covers the occurrence of the term "carbocyclyl" where no numerical range is designated. The carbocyclyl group may also be a medium size carbocyclyl having 3 to 10 carbon atoms. The carbocyclyl group could also be a carbocyclyl having 3 to 6 carbon atoms. The carbocyclyl group may be designated as "$C_{3-6}$ carbocyclyl" or similar designations. Examples of carbocyclyl rings include, but are not limited to, cyclopropyl, cyclobutyl, cyclopentyl, cyclohexyl, cyclohexenyl, 2,3-dihydro-indene, bicycle[2.2.2]octanyl, adamantyl, and spiro[4.4]nonanyl.

A "(carbocyclyl)alkyl" is a carbocyclyl group connected, as a substituent, via an alkylene group, such as "$C_{4-10}$ (carbocyclyl)alkyl" and the like, including but not limited to, cyclopropylmethyl, cyclobutylmethyl, cyclopropylethyl, cyclopropylbutyl, cyclobutylethyl, cyclopropylisopropyl, cyclopentylmethyl, cyclopentylethyl, cyclohexylmethyl, cyclohexylethyl, cycloheptylmethyl, and the like. In some cases, the alkylene group is a lower alkylene group.

As used herein, "cycloalkyl" means a fully saturated carbocyclyl ring or ring system. Examples include cyclopropyl, cyclobutyl, cyclopentyl, and cyclohexyl.

As used herein, "cycloalkenyl" means a carbocyclyl ring or ring system having at least one double bond, wherein no ring in the ring system is aromatic. An example is cyclohexenyl.

As used herein, "heterocyclyl" means a non-aromatic cyclic ring or ring system containing at least one heteroatom in the ring backbone. Heterocyclyls may be joined together in a fused, bridged or spiro-connected fashion. Heterocyclyls may have any degree of saturation provided that at least one ring in the ring system is not aromatic. The heteroatom(s) may be present in either a non-aromatic or aromatic ring in the ring system. The heterocyclyl group may have 3 to 20 ring members (i.e., the number of atoms making up the ring backbone, including carbon atoms and heteroatoms), although the present definition also covers the occurrence of the term "heterocyclyl" where no numerical range is designated. The heterocyclyl group may also be a medium size heterocyclyl having 3 to 10 ring members. The heterocyclyl group could also be a heterocyclyl having 3 to 6 ring members. The heterocyclyl group may be designated as "3-6 membered heterocyclyl" or similar designations. In preferred six membered monocyclic heterocyclyls, the heteroatom(s) are selected from one up to three of O, N or S, and in preferred five membered monocyclic heterocyclyls, the heteroatom(s) are selected from one or two heteroatoms selected from O, N, or S. Examples of heterocyclyl rings include, but are not limited to, azepinyl, acridinyl, carbazolyl, cinnolinyl, dioxolanyl, imidazolinyl, imidazolidinyl, morpholinyl, oxiranyl, oxepanyl, thiepanyl, piperidinyl, piperazinyl, dioxopiperazinyl, pyrrolidinyl, pyrrolidonyl, pyrrolidionyl, 4-piperidonyl, pyrazolinyl, pyrazolidinyl, 1,3-dioxinyl, 1,3-dioxanyl, 1,4-dioxinyl, 1,4-dioxanyl, 1,3-oxathianyl, 1,4-oxathiinyl, 1,4-oxathianyl, 2H-1,2-oxazinyl, trioxanyl, hexahydro-1,3,5-triazinyl, 1,3-dioxolyl, 1,3-dioxolanyl, 1,3-dithiolyl, 1,3-dithiolanyl, isoxazolinyl, isoxazolidinyl, oxazolinyl, oxazolidinyl, oxazolidinonyl, thiazolinyl, thiazolidinyl, 1,3-oxathiolanyl, indolinyl, isoindolinyl, tetrahydrofuranyl, tetrahydropyranyl, tetrahydrothiophenyl, tetrahydrothiopyranyl, tetrahydro-1,4-thiazinyl, thiamorpholinyl, dihydrobenzofuranyl, benzimidazolidinyl, and tetrahydroquinoline.

A "(heterocyclyl)alkyl" is a heterocyclyl group connected, as a substituent, via an alkylene group. Examples include, but are not limited to, imidazolinylmethyl and indolinylethyl.

As used herein, "oxo" refers to =O.

As used herein, "acyl" refers to —C(=O)R, wherein R is hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein. Non-limiting examples include formyl, acetyl, propanoyl, benzoyl, and acryl.

An "O-carboxy" group refers to a "—OC(=O)R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

A "C-carboxy" group refers to a "—C(=O)OR" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein. A non-limiting example includes carboxyl (i.e., —C(=O)OH).

A "cyano" group refers to a "—CN" group.

A "cyanato" group refers to an "—OCN" group.

An "isocyanato" group refers to a "—NCO" group.

A "thiocyanato" group refers to a "—SCN" group.

An "isothiocyanato" group refers to an "—NCS" group.

A "sulfinyl" group refers to an "—S(=O)R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

A "sulfonyl" group refers to an "—SO$_2$R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "S-sulfonamido" group refers to a "—SO$_2$NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-sulfonamido" group refers to a "—N(R$_A$)SO$_2$R$_B$" group in which R$_A$ and R$_b$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "O-carbamyl" group refers to a "—OC(=O)NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-carbamyl" group refers to an "—N(R$_A$)C(=O) OR$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "O-thiocarbamyl" group refers to a "—OC(=S) NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-thiocarbamyl" group refers to an "—N(R$_A$)C(=S) OR$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

A "C-amido" group refers to a "—C(=O)NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-amido" group refers to a "—N(R$_A$)C(=O)R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "amino" group refers to a "—NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein. A non-limiting example includes free amino (i.e., —NH$_2$).

An "aminoalkyl" group refers to an amino group connected via an alkylene group.

An "alkoxyalkyl" group refers to an alkoxy group connected via an alkylene group, such as a "$C_{2-8}$ alkoxyalkyl" and the like.

As used herein, a substituted group is derived from the unsubstituted parent group in which there has been an exchange of one or more hydrogen atoms for another atom or group. Unless otherwise indicated, when a group is deemed to be "substituted," it is meant that the group is substituted with one or more substituents independently selected from $C_1$-$C_6$ alkyl, $C_1$-$C_6$ alkenyl, $C_1$-$C_6$ alkynyl, $C_1$-$C_6$ heteroalkyl, $C_3$-$C_7$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$) alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, cyano, hydroxy, $C_1$-$C_6$ alkoxy, $C_1$-$C_6$ alkoxy($C_1$-$C_6$)alkyl (i.e., ether), aryloxy, sulfhydryl (mercapto), halo($C_1$-$C_6$) alkyl (e.g., —CF$_3$), halo($C_1$-$C_6$)alkoxy (e.g., —OCF$_3$), $C_1$-$C_6$ alkylthio, arylthio, amino, amino($C_1$-$C_6$)alkyl, nitro, O-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, and oxo (=O). Wherever a group is described as "optionally substituted" that group can be substituted with the above substituents.

It is to be understood that certain radical naming conventions can include either a mono-radical or a di-radical, depending on the context. For example, where a substituent requires two points of attachment to the rest of the molecule, it is understood that the substituent is a di-radical. For example, a substituent identified as alkyl that requires two points of attachment includes di-radicals such as —CH$_2$—, —CH$_2$CH$_2$—, —CH$_2$CH(CH$_3$)CH$_2$—, and the like. Other radical naming conventions clearly indicate that the radical is a di-radical such as "alkylene" or "alkenylene."

When two R groups are said to form a ring (e.g., a carbocyclyl, heterocyclyl, aryl, or heteroaryl ring) "together with the atom to which they are attached," it is meant that the collective unit of the atom and the two R groups are the recited ring. The ring is not otherwise limited by the definition of each R group when taken individually. For example, when the following substructure is present:

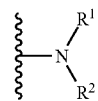

and R$^1$ and R$^2$ are defined as selected from the group consisting of hydrogen and alkyl, or R$^1$ and R$^2$ together with the nitrogen to which they are attached form a heteroaryl, it is meant that $R^1$ and $R^2$ can be selected from hydrogen or alkyl, or alternatively, the substructure has structure:

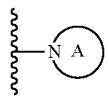

where ring A is a heteroaryl ring containing the depicted nitrogen.

Similarly, when two "adjacent" R groups are said to form a ring "together with the atoms to which they are attached," it is meant that the collective unit of the atoms, intervening bonds, and the two R groups are the recited ring. For example, when the following substructure is present:

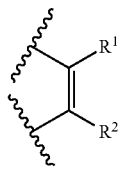

and $R^1$ and $R^2$ are defined as selected from the group consisting of hydrogen and alkyl, or $R^1$ and $R^2$ together with the atoms to which they are attached form an aryl or carbocyclyl, it is meant that $R^1$ and $R^2$ can be selected from hydrogen or alkyl, or alternatively, the substructure has structure:

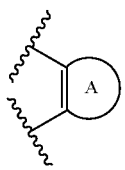

where A is an aryl ring or a carbocyclyl containing the depicted double bond.

Wherever a substituent is depicted as a di-radical (i.e., has two points of attachment to the rest of the molecule), it is to be understood that the substituent can be attached in any directional configuration unless otherwise indicated. Thus, for example, a substituent depicted as—AE—or

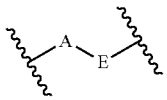

includes the substituent being oriented such that the A is attached at the leftmost attachment point of the molecule as well as the case in which A is attached at the rightmost attachment point of the molecule.

"Leaving group," or "LG," as used herein refers to any atom or moiety that is capable of being displaced by another atom or moiety in a chemical reaction. More specifically, in some embodiments, "leaving group" refers to the atom or moiety that is displaced in a nucleophilic substitution reaction. In some embodiments, "leaving groups" are any atoms or moieties that are conjugate bases of strong acids. Examples of suitable leaving groups include, but are not limited to, tosylates and halogens. Non-limiting characteristics and examples of leaving groups can be found, for example in Organic Chemistry, 2d ed., Francis Carey (1992), pages 328-331; Introduction to Organic Chemistry, 2d ed., Andrew Streitwieser and Clayton Heathcock (1981), pages 169-171; and Organic Chemistry, 5th ed., John McMurry (2000), pages 398 and 408; all of which are incorporated herein by reference for the limited purpose of disclosing characteristics and examples of leaving groups.

Unless defined otherwise, all technical and scientific terms used herein have the same meaning as commonly understood by one of ordinary skill in the art to which the embodiments belong. Although any methods and materials similar or equivalent to those described herein can also be used in the practice or testing of the embodiments, the preferred methods and materials are now described. All publications mentioned herein are incorporated herein by reference to disclose and describe the methods and/or materials in connection with which the publications are cited.

Protecting Groups

In some circumstances, a chemical reaction may need to be performed selectively at one reactive site in a multifunctional compound. One such method that is useful for accomplishing such selectivity is to temporarily block one or more reactive sites in the multifunctional compound with a protective group. Such a method is often referred to as "protecting" the functional group. Many protecting groups are known in the art. See, e.g., Greene et al., Protective Groups in Organic Synthesis, Third Ed. (John Wiley & Sons, Inc. 1999), herein incorporated by reference in its entirety; Wutz et al., Greene's Protective Groups in Organic Synthesis, Fourth Ed. (John Wiley & Sons, Inc. 2007), herein incorporated by reference in its entirety. When more than one reactive site in a multifunctional compound requires protecting, or when a compound is prepared that will possess more than one protected functional group, it is important to use orthogonal protecting groups. Protecting groups are orthogonal if they are susceptible to selective removal.

In some embodiments, it may be necessary to protect one or more functional groups so as to prevent their interference in the desired reaction. For example, it may be necessary to protect one or more functional groups such as amines, carboxylic acids, and/or hydroxyl groups.

Suitable protecting groups for protecting amines include: carbamates such as alkyl carbamates including methyl, ethyl, propyl, isopropyl, butyl, tert-butyl, sec-butyl, pentyl, neopentyl, hexyl, heptyl, nonnyl, decanyl, and configurational isomers thereof; 9-flurenylmethyl; 9-(2-sulfo)flurenylmethyl; 9-(2,7-dibromo)fluorenylmethyl; 17-tetrabenzo[a,c,g,i]flurenylmethyl; 2-chloro-3-indenylmethyl; benz[f]inden-3-ylmethyl; 2,7-di-t-butyl[9-(10,10-dioxo-10,10,10,10-tetrahydrothioxanthyl)]methyl; 1,1-dioxobenzo[b]thiophene-2-ylmethyl; substituted ethyl carbamates such as 2,2,2-trichloroethyl; 2-trimethylsilylethyl; 2-phenylethyl; 1-(1-adamantyl)-1-methylethyl; 2-chloroethyl; 1,1-dimethyl-2-haloethyl; 1,1-dimethyl,2,2-dibromoethyl; 1,1-dimethyl-2,2,2-trichloroethyl; 1-methyl-1-(4-biphenylyl)ethyl; 1-(3,5-di-t-butylphenyl)-1-methylethyl; 2-(2'- and 4'-prydyl) ethyl; N-(2-pivaloylamino)-1,1-dimethylethyl; 2-[(2-nitrophenyl)dithio]-1-phenylethyl; 2-(N,N,-dicyclohexylcarboxamido)ethyl; t-butyl; 1-adamantyl; 2-adamantyl; vinyl; allyl; 1-isopropylallyl; cinnamyl; 4-nitrocinnamyl; 3-(3'-pyridyol) prop-2-enyl; 8-quinolyl; N-hydroxypiperidinyl; alkydithio; benzyl; p-methoxybenzyl; p-nitrobenzykl; p-bromobenzyl; p-chlorobenzyl; 2,4-dichlorobenzyl; 4-methylsulfinylbenzyl; 9-anthrylmethyl; diphenylmethyl; 2-methylthioethyl;

2-methylsulfonylethyl; 2-(p-toluenesulfonyl)ethyl; [2-(1,3-dithianyl)]methyl; 4-methylthiophenyl; 2,4-dimethylthiophenyl; 2-phosphonioethyl; 1-methyl-1-(triphenylphosphonio) ethyl; 1,1-dimethyl-2-cyanoethyl; 2-dansylethyl; 2-(4-nitrophenyl)ethyl; 4-phenylacetoxybenzyl; 4-azidobenzyl; 4-azidomethoxybenzyl; m-chloro-p-acyloxybenzyl; p-(dihydroxyboryl)benzyl; 5-benzisoxazolylmethyl; 2-(trifluoromethyl)-6-chromonylmethyl; m-nitrophenyl; 3,5-dimethoxybenzyl; 1-methyl-1-(3,5-dimethoxyphenyl)ethyl; α-methylnitropiperonyl; o-nitrobenzyl; 3,4-dimethoxy-6-nitrobenzyl; phenyl(o-nitrophenyl)methyl; 2-(2-nitrophenyl) ethyl; 6-nitroveratryl; 4-methoxyphenacyl; 3',5'-dimethoxybenzoin; phenothiazinyl-(10)-carbonyl derivatives; N'-p-toluenesulfonylaminocarbonyl; N'-phenylaminothiocarbonyl; t-amyl; S-benzyl thiocarbamate; butynyl; p-cyanobenzyl; cyclobutyl; cyclohexyl; cyclopentyl; cyclopropylmethyl; p-dicyloxybenzyl; diisopropylmethyl; 2,2-dimethoxycarbonylvinyl; o-(N',N'-dimethylcarboxamido)benzyl; 1,1-dimethyl-3-(N',N'-dimethylcarboxamido)propyl; 1,1-dimethylpropynyl; di(2-pyridyl)methyl; 2-furanylmethyl; 2-iodoethyl; isobornyl; isobutyl; isonicotinyl; p-(p'-methoxyphenylazo)benzyl; 1-methylcyclobutyl; 1-methylcyclohexyl; 1-methyl-1-cyclopropylmethyl; 1-methyl-1-(p-phenylazophenyl)ethyl; 1-methyl-1-phenylethyl; 1-methyl-1-(4'-pyridyl)ethyl; phenyl; p-(phenylazo)benzyl; 2,4,6-tri-t-butylphenyl; 4-(trimethylammonium)benzyl; 2,4,6-trimethylbenzyl; and other similar carbamates; amides, including, but not limited to, formyl, acetyl, chloroacetyl, trichloroacetyl, trifluoroacetyl, phenylacetyl, propionyl, 3-phenylpropionyl, 4-pentenoyl, picolinoyl, 3-pyridylcarboxamide, benzoylphenylalanyl, benzoyl, p-phenylbenzoyl, amides whose cleavage is induced by nitro group reduction, such as o-nitrophenylacetyl, o-nitrophenoxyacetyl, 3-(o-nitrophenyl)propionyl, 2-methyl-2-(o-nitrophenoxy)propionyl, 3-methyl-3-nitrobutyryl, o-nitrocinnamoyl, o-nitrobenzoyl, and 3-(4-t-butyl-2,6-dinitrophenyl)-2,2-dimethylpropionyl; amides whose cleavage is induced by release of an alcohol, such as o-(benzoyloxymethyol)benzoyl, (2-acetoxymethyl)benzoyl, 2-[(t-butyldiphenylsiloxy)methyl]benzoyl, 3-(3',6'-dioxo-2', 4',5'-trimethylcyclohexa-1',4'-diene-3,3-dimethylpropionyl, and o-hydroxy-trans-cinnamoyl; amides whose cleavage is induced by other chemical reactions, such as 2-methyl-2-(o-phenylazophenoxy)propionyl, 4-chlorobutyryl, acetoacetyl, 3-(p-hydroxyphenyl)propionyl, (N'-dithiobenzyloxycarbonylamino)acetyl, N-acetylmethionine, and 4,5-diphenyl-3-oxazolin-2-one; cyclic imide derivatives such as N-phthaloyl, N-tetrachlorophthaloyl, N-4-nitrophthaloyl, N-dithiasuccinoyl, N-2,3-diphenylmaleoyl, N-2,5-dimethylpyrrolylN-2,5-bis(triisopropylsiloxy)pyrrolyl, N-1,1,4,4,-tetramethyldisilylazacyclopentane adduct, N-1,1,3,3,-tetramethyl-1,3-disilaisoindolyl, 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridonyl, and 1,3,5-dioxazinyl; N-alkyl and N-aryl derivatives, such as N-methyl, N-t-butyl, N-allyl, N-[2-(trimethylsilyl)ethoxy]methyl, N-3-acetoxypropyl, N-cyanomethyl, N-(1-isopropyl-4-nitro-2-oxo-3-pyrrolin-3-yl), N-2,4-dimethoxybenzyl, N-2-azanorbornenyl, N-2,4-dinitrophenyl, quaternary ammonium salts, N-benzyl, N-4-methoxybenzyl, N-2,4-dimethoxybenzyl, N-2-hydroxybenzyl, N-diphenylmethyl, N-bis(4-methoxyphenyl)methyl, N-5-dibenzosuberyl, N-triphenylmethyl, N-(4-methoxyphenyl)duiphenylmethyl, N-9-phenylfluorenyl, N-ferrocenylmethyl, and N-2-picolylamine N'-oxide; imine derivatives, such as N-1,1-dimethylthiomethylene, N-benzylidene, N-p-methoxybenzylidine, N-diphenylmethylene, N-[(2-pyridyl) mesityl]methylene, N—(N',N'-dimethylaminomethylene), N—(N',N'-dibenzylaminomethylene), N—(N'-t-butylaminomethylene), N,N'-isopropylidene, N-p-nitrobenzylidene, N-salicylidene, N-5-chlorosalicylidene, N-(5-chloro-2-hydroxyphenyl)phenylmethylene, N-cyclohexylidene, and N-t-butylidene; enamine derivatives, such as N-(5,5-dimethyl-3-oxo-1-cyclohexenyl), N-2,7-dichloro-9-fluorenylmethylene, N-2-(4,4-dimethyl-2,6-dioxocyclohexylidene) ethyl, N-4,4,4-trifluoro-3-oxo-1-butenyl, and N-1-isopropyl-4-nitro-2-oxo-3-pyrrolin-3-yl; and N-heteroatom derivatives such as N-metal, N-borane, N-diphenylborinic acid, N-diethylborinic acid, N-diflorobornic acid, N,N'-3,5-bis(trifluoromethyl)phenylboronic acid, N-[phenyl(pentacarbonylchromium-or-tungsten)]carbonyl, N-copper chelates, N-zinc chelates, and 18-crown-6 derivatives, N—N derivatives such as N-nitro, N-nitroso, N-oxide, and triazene derivatives, N—P derivatives such as N-diphenylphosphinyl, N-dimethylthiophosphinyl, N-diphenylthiophosphinyl, N-dialkylphosphoryl, N-dibenzylphosphoryl, N-diphenylphosphoryl, and iminotriphenylphosphorane derivatives, N—Si derivatives, N-sulfenyl derivatives such as N-benzenesulfonyl, N-o-nitrobenzenesulfenyl, N-2,4-dinitrobenzenesulfenyl, N-pentachlorobenzenesulfenyl, N-2-nitro-4-methoxybenzenesulfenyl, N-triphenylmethylsulfenyl, N-1-(2,2,2-trifluoro-1,1-diphenyl)ethylsulfenyl, and N-3-nitro-2-pyridinesulfenyl, and/or N-sulfonyl derivatives such as N-p-toluenesulfonyl, N-benzenesulfonyl, N-2,3,6-trimethyl-4-methoxybenzenesulfonyl, N-2,4,6-trimethoxybenzenesulfonyl, N-2,6-dimethyl-4-methoxybenzenesulfonyl, N-pentamethylbenzenesulfonyl, N-2,3,5,6-tetramethyl-4-methoxybenzenesulfonyl, N-4-methoxybenzenesulfonyl, N-2,4,6-trimethylbenzenesulfonyl, N-2,6-dimethoxy-4-methylbenzenesulfonyl, N-3-methoxy-4-t-butylbenzenesulfonyl, N-2,2,5,7,8-pentamethylchroman-6-sulfonyl, N-2-nitrobenzenesulfonyl, N-4-nitrobenzenesulfonyl, N-2,4-dinitrobenzenesulfonyl, N-benzothiazole-2-sulfonyl, N-methanesulfonyl, N-2-(trimethylsilyl)ethanesulfonyl, N-9-anthracenesulfonyl, N-4-(4', 8'-dimethoxynaphthylmethyl)benzenesulfonyl, N-benzylsulfonyl, N-trifluoromethylsulfonyl, N-phenacylsulfonyl, and N-t-butylsulfonyl.

Suitable protecting groups for carboxylic acids include: esters such as enzymatically cleavable esters including heptyl, 2-N-(morpholino)ethyl, choline, (methoxyethoxy)ethyl, methoxyethyl; alkyl esters such as methyl, ethyl, propyl, isopropyl, butyl, tert-butyl, sec-butyl, pentyl, neopentyl, hexyl, heptyl, nonnyl, decanyl, and configurational isomers thereof; substituted methyl esters such as 9-fluroenylmethyl, methoxymethyl, methylthiomethyl, tetrahydropyranyl, teatrahydrofuranyl, methoxyethoxymethyl, 2-(trimethylsilyl)ethoxymethyl, benzyloxymethyl, pivaloyloxymethyl, phenylacetoxymethyl, triisopropylsilylmethyl, cyanomethyl, acetol, phencacyl, p-bromophenacyl, α-methylphenacyl, p-methoxyphenacyl, desyl, carboamidomethyl, p-azobenzenecarboxamidomethyl, N-phthalidimdomethyl; 2-substituted ethyl esters such as 2,2,2-trichloroethyl, 2-haloethyl, ω-chloroalkyl, 2-(trimethylsilyl)ethyl, 2-methylthioethyl, 1,3-dithianyl-2-methyl, 2-(p-nitrophenylsulfenyl) ethyl, 2-(p-toluenesulfonyl)ethyl, 2-(2'-pyridyl)ethyl, 2-(p-methoxyphenyl)ethyl, 2-(diphenylphosphino)ethyl, 1-methyl-1-phenylethyl, 2-(4-acetyl-2-nitrophenyl)ethyl, 2-cyanoethyl, 3-methyl-3-pentyl, dicyclopropylmethyl, 2,4-dimethyl-3-pentyl, cyclopentyl, cyclohexyl, allyl, methallyl, 2-methylbut-e-en-2-yl, 3-methylbut-2-(prenyl), 3-buten-1-yl, 4-(trimethylsilyl)-2-buten-1-yl, cinnamyl, α-methylcinnamyl, prop-2-ynyl, phenyl; 2,6-dialkylphenyl esters such as 2,6-dimethylphenyl, 2,6-diisopropylphenyl, 2,6-di-t-butyl- 4-methylphenyl, 2,6-di-t-butyl-4-methoxyphenyl, p-(methylthio)phenyl, pentafluorophenyl, benzyl; substituted benzyl esters such as triphenylmethyl, diphenylmethyl, bis(o-nitrophenyl)methyl, 9-anthrylmethyl, 2-(9,10-dioxo)anthrylmethyl, 5-dibenzosuberyl, 1-pyreneylmethyl, 2-(trifluoromethyl)-6-chromonylmethyl, 2,4,6-trimethylbenzyl, p-bromobenzyl, o-nitrobenzyl, p-nitrobenzyl, p-methoxybenzyl, 2,6-dimethoxybenzyl, 4-(methylsulfinyl)benzyl, 4-sulfobenzyl, 4-azidomethoxybenzyl, 4-{N-[1-(4,4-dimethyl-2,6-dioxocyclohexylidene)-3-methylbutyl] amino}benzyl, piperonyl, 4-picolyl, polymer supported p-benzyl; silyl esters such as trimethylsilyl, triethylsilyl, t-butyldimethylsilyl, i-propyldimethylsilyl, phenyldimethylsilyl, di-t-butylmethylsilyl, triisopropylsilyl; activated esters such as thiol esters; oxazoles; 2-alkyl-1,3-axazoline; 4-alkyl-5-oxo-1,3-oxazolidine; 2,2-bistrifluoromethyl-4-alkyl-5-oxo-1,3-oxazolidine; 5-alkyl-4-oxo-1,3-dioxolane; dioxanones; ortho esters; pentaaminocobalt(III) complexes; and stannyl esters such as triethylstannyl and tri-n-butylstannyl; amides such as N,N-dimethyl, pyrrolidinyl, piperidinyl, 5,6-dihydrophenanthridinyl, o-nitroanilide, N-7-nitroindolyl, N-8-nitro-1,2,3,4-tetrahydroquinolyl, 2-(2-aminophenyl)acetaldehyde dimethyl acetal amide, and polymer supported p-benzenesulfonamide; hydrazides such as N-phenyl, N,N'diisopropyl; and tetraalkylammonium salts such as methyl, ethyl, propyl, isopropyl, butyl, tert-butyl, sec-butyl, pentyl, neopentyl, hexyl, heptyl, nonnyl, decanyl, and configurational isomers thereof.

Suitable protecting groups for hydroxyl groups include: silyl ethers such as trimethylsilyl, triethylsilyl, triisopropylsilyl, dimethylisopropylsilyl, diethylisopropylsilyl, dimethylthexylsilyl, 2-norbornyldimethylsilyl, t-butyl-dimethylsilyl, t-butyldiphenylsilyl, tribenzylsilyl, tri-p-xylylsilyl, triphenylsilyl, diphenylmethylsilyl, di-t-butylmethylsilyl, bis(t-butyl)-1-pyrenylmethoxysilyl, tris(trimethylsilyl)silyl: sisyl; (2-hydroxystyryl)dimethylsilyl; (2-hydroxystyryl)diisopropylsilyl, t-butylmethoxyphenylsilyl, t-butoxydiphenylsilyl, 1,1,3,3-tetraisopropyl-3-[2-(triphenylmethoxy) ethoxy]disiloxane-1-yl, fluorous silyl; $C_{1-10}$alkyl ethers such as methyl, ethyl, propyl, isopropyl, butyl, tert-butyl, sec-butyl, pentyl, neopentyl, hexyl, heptyl, nonnyl, decanyl, and configurational isomers thereof; substituted methyl ethers such as methoxymethyl, methylthiomethyl, (phenyldimethylsilyl)methoxymethyl, benzyloxymethyl, p-methoxybenzyloxymethyl, [(3,4-dimethoxybenzyl)oxy]methyl, p-nitrobenzyloxymethyl, o-nitrobenzyloxymethyl, [(R)-1-(2-nitrophenyl)ethoxy]methyl, (4-methoxyphenoxy)methyl, guaiacolmethyl, t-butoxymethyl, 4-pentenyloxymethyl, siloxymethyl, 2-methoxyethoxymethyl, 2-cyanoethoxymethyl, 2,2,2-trichloroethoxymethyl, bis(2-chloroethoxy) methyl, 2-(trimethylsilyl)ethoxymethyl, methoxymethyl, O-Bis(2-acetoxyethoxy)methyl, tetrahydropyranyl, fluorous tetrahydropyranyl, 3-bromotetrahydropyranyl, tetrahydrothiopyranyl, 1-methoxycyclohexyl, 4-methoxytetrahydropyranyl, 4-methoxytetrahydrothiopyranyl, 4-methoxytetrahydrothiopyranyl S,S-dioxide, 1-[(2-chloro-4-methyl)phenyl]-4-methoxypiperidin-4-yl, 1-(2-fluorophenyl)-4-methoxypiperidin-4-yl, 1-(4-chlorophenyl)-4-methoxypiperidin-4-yl, 1,4-dioxan-2-yl, tetrahydrofuranyl, tetrahydrothiofuranyl, and 2,3,2a,4,5,6,7,7a-octahydro-7,8, 8-trimethyl-4,7-methanobenzofuran-2-yl; substituted ethyl ethers such as 1-ethoxyethyl, 1-(2-chloroethoxy)ethyl, 2-hyddroxyethyl, 2-bromoethyl, 1-[2-(trimethylsilyl) ethoxy]ethyl, 1-methyl-1-methoxyethyl, 1-methyl-1benzyloxyethyl, 1-methyl-1-benzyloxy-2-fluoroethyl, 1-methyl-1-phenoxyethyl, 2,2,2-trichloroethyl, 1,1-dianisyl-2,2,2-trichloro ethyl, 1,1,1,3,3,3-hexafluoro-2-phenylisopropyl, 1-(2-cyanoethoxy)ethyl, 2-trimethylsilylethyl, 2-(benzylthio)ethyl, 2-(phenylselenyl)ethyl, t-butyl, allyl, prennyl, cinnamyl, 2-phenallyl, propargy, p-chlorophenyl, p-methoxyphenyl, p-nitrophenyl, 2,4-dinitrophenyl, 2,3,5,6-tetrafluoro-4-(trifluoromethyl)phenyl; benzyl; substituted benzyl ethers such as p-methoxybenzyl, 3,4-dimethoxybenzyl, o-nitrobenzyl, p-nitrobenzyl, pentadienylnitrobenzyl, pentadienylnitropiperonyl, halobenzyl, 2,6-dichlorobenzyl, 2,4-dichlorobenzyl, p-cyanobenzyl, p-phenylbenzyl, 2,6-difluorobenzyl, fluorous benzyl, 4-fluorousalkoxybenzyl, trimethylsilylxylyl, 2-phenyl-2-propyl (Cumyl), p-acylaminobenzyl, p-azidobenzyl, 4-azido-3-chlorobenzyl, 2-trifluoromethylbenzyl, 4-trifluromethylbenzyl, p-(methylsulfinyl)benzyl, p-siletanylbenzyl, 4-acetoxybenzyl, 4-(2-trimethylsilyl)ethoxymethoxybenzyl, 2-napthylmethyl, 2-picolyl, 4-picolyl, 3-methyl-2-picolyl N-oxido, 2-quinolinylmethyl, 6-methoxy-2-(4-methylphenyl)-4-quinolinemethyl, 1-pyrenylmethyl, diphenylmethyl, 4-methoxydiphenylmethyl, 4-phenyldiphenylmethyl, p,p'-dinitrobenzhydryl, 5-dibenzosuberyl, triphenylmethyl, α-napthyldiphenylmethyl, p-methoxyphenyldiphenylmethyl, di(p-methoxyphenyl)phenylmethyl, tri(p-methoxyphenyl)methyl, 4-(4'-bromophenacyloxy)phenyldiphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 4,4'-dimethoxy-3"-[N-imidazolylmethyl)]trityl, 4,4'-dimethoxy-3"-[N-imidazolylethyl)carbamoyl]trityl, 1,1-bis(4-methoxyphenyl)-1'-pyrenylmethyl, 4-(17-tetrabenzo[a,c,g,i] fluorenylmethyl)-4,4"-dimethoxytrityl, 9-anthryl, 9-(9-phenyexanthenyl, 9-phenylthioxanthyl, 9-(9-phenyl-10-oxo)anthryl, 1,3-benzodithiolan-2-yl, 4,5-bis (ethoxycarbonyl)-[1,3]-dioxolan-2-yl, benzisothiazolyl S,S-dioxido; $C_{1-10}$alkyl esters such as formyl, acetyl, propionyl, isopropionyl, butyryl, tert-butyryl, sec-butyryl, pentanoyl, neopentanoyl, hexanoyl, heptanoyl, nonanoyl, decanoyl, and configurational isomers thereof, esters such as benzoylformate, chloroacetate, dichloroacetate, trichloroacetate, trifluoroacetate, methoxyacetate, triphenylmethoxyacetate, phenoxyacetate, p-chlorophenoxyacetate, phenylacetate, polymer supported p-phenylacetate, diphenylacetate, bisfluorous chain type propanoyl, nicotinate, 3-phenylpropionate, 4-pentenoate, 4-oxopentanoate, 4,4-(ethylenedithio) pentanoate, 5-[3-bis(4-methoxyphenyl) hydroxymethylphenoxy]levulinate, pivaloate, 1-adamantoate, crotonate, 4-methoxycrotonate, benzoate, p-phenylbenzoate, 2,4,6-trimethylbenzoate, picolinate, nicotinate, 4-bromobenzoate, 2,5-difluorobenzoate, p-nitrobenzoate, 2,6-dichloro-4-methylphenoxyacetate, 2,6-dichloro-4-(1,1,3,3-tetramethylbutyl)phenoxyacetate, 2,4-bis (1,1-dimethylpropyl)phenoxyacetate, chlorodiphenylacetate, isobutyrate, monosuccinoate, 2-methyl-2-butenoate, (E)-2-methyl-2-butenoate, (Z)-2-methyl-2-butenoate, o-(methoxycarbonyl)benzoate, polymer supported p-benzoate, α-naphthoate, nitrate, alkyl N,N,N',N'-tetramethylphosphorodiamidate, 2-chlorobenzoate, 3',5'-dimethoxybenzoin, N-phenylcarbamate, borate, dimethylphosphinothioyl, 2,4-dinitrophenylsulfenate, and photolabile esters; carbonates, including methyl, methoxymethyl, 9-fluorenylmethyl, ethyl, 2,2,2-trichloroethyl, 1,1-dimethyl-2,2,2-trichloroethyl, 2-(trimethylsilyl)ethyl, 2-(triphenylsulfonyl)ethyl, 2-(triphenylphosphonia)ethyl, isobutyl, vinyl, allyl, p-nitrophenyl, benzyl, p-methoxybenzyl, 3,3-dimethoxybenzyl, o-nitrobenzyl, p-nitrobenzyl, and silyl esters; carbonates cleaved by β-elimination such as 2-dansylethyl, 2-(4-nitrophenyl)ethyl, 2-(2,4-dinitrophenyl) ethyl, 2-cyano-1-phenylethyl, S-benzyl thiocarbonate, 4-ethoxy-1-mapthyl, and methyl dithiocarbonate, carbonates cleaved with assisted cleavage such as 2-iodobenzoate, 4-azidobutyrate, 4-nitro-4-methylpentanoate, o-(dibromomethyl)benzoate, 2-formylbenzenesulfonate, 2-(methylthiomethyoxy)ethyl, 4-(methylthiomethoxymethyl)butyrate, 2-(methylthiomethoxymethyl)benzoate, 2-(chloroacetoxymethyl)benzoate, 2-[(2-chloroacetoxy)ethyl]benzoate, 2-[2-(benzyloxy)ethyl]benzoate, 2-[2-(4-methoxybenzyloxy)ethyl]benzoate; and sulfonates such as sulfate, allylsulfate, $C_{1-10}$alkyl sulfonates such as methyl, ethyl, propyl, isopropyl, butyl, tert-butyl, sec-butyl, pentyl, neopentyl, hexyl, heptyl, nonnyl, decanyl, and configurational isomers thereof, benzylsulfonate, tosylate, and 2-[(4-nitrophenyl)ethyl]sulfonate.

Protection and Deprotection Reactions

Reagents, solvents, and reaction conditions useful for protecting amines, carboxylic acids, and alcohols are well-known in the art. Likewise, reagents, solvents, and reaction conditions useful for deprotecting amines, carboxylic acids, and alcohols are well known in the art. See, e.g., Greene et al., Protective Groups in Organic Synthesis, Third Ed. (John Wiley & Sons, Inc. 1999), herein incorporated by reference in its entirety; Wutz et al., Greene's Protective Groups in Organic Synthesis, Fourth Ed. (John Wiley & Sons, Inc. 2007), herein incorporated by reference in its entirety. While references have been made to specific reagents, solvents, and reaction conditions in the schemes described above, it is readily envisioned that equivalent reagents, solvents, and reaction conditions may be utilized to protect and deprotect amines, carboxylic acids, and alcohols.

Intermediate Compounds

Some embodiments disclosed herein include intermediates in the synthetic methods described herein, including a compound having the structure of Formula (I):

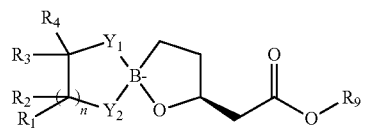

or a salt thereof.

In some embodiments, $R_1$ and $R_2$ are independently selected from the group consisting of H, optionally substituted phenyl and optionally substituted $C_{1-4}$ alkyl, or $R_1$ and $R_2$ together with the atoms to which they are attached, form =O.

In some embodiments, $R_3$ is selected from the group consisting of H, optionally substituted phenyl and optionally substituted $C_{1-4}$ alkyl, $R_3$ and $R_5$ together with the atoms to which they are attached form heteroaryl ring, or $R_3$ and $R_4$ together with the atoms to which they are attached, form =O.

In some embodiments, $R_4$ is selected from the group consisting of H, optionally substituted phenyl, optionally substituted $C_{1-4}$ alkyl, or $R_3$ and $R_4$ together with the atoms to which they are attached, form =O.

In some embodiments, $R_5$, $R_6$, and $R_{10}$ are independently selected from the group consisting of H, optionally substituted phenyl and optionally substituted $C_{1-4}$ alkyl.

In some embodiments, $R_9$ is selected from the group consisting of optionally substituted $C_1$-$C_{12}$ alkyl, optionally substituted $C_3$-$C_8$ cycloalkyl, optionally substituted $C_2$-$C_{12}$ alkenyl, optionally substituted $C_2$-$C_{12}$ alkynyl, optionally substituted aryl and optionally substituted heteroaryl.

In some embodiments, independently, two germinal $R_1$, $R_2$, $R_3$, and $R_4$ together with the atoms to which they are attached, form =O.

In some embodiments, $Y_1$ is O. In some embodiments, $Y_1$ is $N^+R_5R_6$.

In some embodiments, $Y_2$ is O. In some embodiments, $Y_2$ is $NR_{10}$.

In some embodiments, n is 0. In some embodiments, n is 1.

In some embodiments, $R_1$, $R_2$, $R_3$, $R_4$, $R_5$, and $R_6$, are hydrogen.

In some embodiments, $R_1$ is optionally substituted phenyl. In some embodiments, $R_1$ is optionally substituted $C_1$-$C_4$ alkyl. In some embodiments, $R_2$ is optionally substituted phenyl. In some embodiments, $R_2$ is optionally substituted $C_1$-$C_4$ alkyl. In some embodiments $R_1$ and $R_2$, together with the atoms to which they are attached, form =O. In some embodiments $R_1$ and $R_3$, together with the atoms to which they are attached, form a carbocyclic ring In some embodiments, $R_3$ is optionally substituted phenyl. In some embodiments, $R_3$ is optionally substituted $C_1$-$C_4$ alkyl. In some embodiments, $R_4$ is optionally substituted phenyl. In some embodiments, $R_4$ is optionally substituted $C_1$-$C_4$ alkyl. In some embodiments, $R_5$ is optionally substituted phenyl. In some embodiments, $R_5$ is optionally substituted $C_1$-$C_4$ alkyl. In some embodiments, $R_6$ is optionally substituted phenyl. In some embodiments, $R_6$ is optionally substituted $C_1$-$C_4$ alkyl. In some embodiments $R_3$ and $R_5$, together with the atoms to which they are attached, form a heteroaryl ring.

In some embodiments, $R_9$ is optionally substituted $C_1$-$C_{12}$ alkyl. In some embodiments, $R_9$ is t-butyl. In some embodiments, $R_9$ is optionally substituted $C_3$-$C_8$cycloalkyl. In some embodiments, $R_9$ is optionally substituted $C_2$-$C_{12}$ alkenyl. In some embodiments, $R_9$ is optionally substituted $C_2$-$C_{12}$ alkynyl. In some embodiments, $R_9$ is optionally substituted aryl. In some embodiments, $R_9$ is optionally substituted heteroaryl.

In some embodiments, $R_{10}$ is H. In some embodiments, $R_{10}$ is optionally substituted phenyl. In some embodiments, $R_{10}$ is optionally substituted $C_{1-4}$ alkyl.

In some embodiments, each $C_{1-4}$ alkyl is optionally substituted with one or more substituents independently selected from the group consisting of, OMe, and phenyl. In some embodiments, each $C_{1-4}$ alkyl is optionally substituted with OMe. In some embodiments, each phenyl is optionally substituted with one to three substitutions independently selected from the group consisting of OMe, and halogen.

In some embodiments, each phenyl is optionally substituted with OMe. In some embodiments, each phenyl is optionally substituted with halogen.

Some specific embodiments of the compound described herein have the following structures:

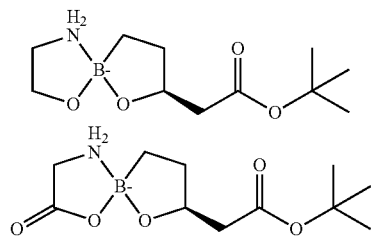

-continued

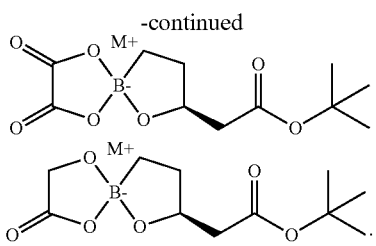

In some embodiments, M⁺ is a metal cation. In some embodiments, M⁺ is a non-metal cation. In some embodiments, M⁺ and the compound of Formula (I) are in a 1:1 ratio. In some embodiments, M⁺ and the compound of Formula (I) are in a ratio between 1:10 and 10:1. Non-limiting examples of M⁺ include cations of lithium, sodium, potassium, calcium, ammonia, triethylamine, and aluminum.

Intermediate compounds of Formula (I) have the advantageous property of being crystalline, thus facilitating purification. More particularly, crystalline intermediates of Formula (I) are advantageous because no chromatography is required to remove impurities and excess reagents. For example, metal catalysts and other borane reagents would normally necessitate silica gel chromatography prior to entering the next step in the synthesis of therapeutic boronate beta-lactamase inhibitors. In some embodiments, intermediate compounds of Formula (I) are filtered, washed with suitable solvent, and carried onto the next synthetic step without further purification. In some embodiments, suitable solvents include dimethyl ether, diethyl ether, diisopropyl ether, MTBE, ACN, THF, DCM, chloroform, ethyl acetate, pentanes, hexanes, heptanes, petroleum ether, benzene, toluene, trifluorotoluene, acetone, 2-Me-THF, CPME, 2-butanone, 1,2-dichloroethane, dioxane, pyridine, o-xylene, m-xylene, p-xylene, or any combination thereof.

Methods of Preparation

The compounds disclosed herein may be synthesized by methods described below, or by modification of these methods. Ways of modifying the methodology include, among others, temperature, solvent, reagents etc., known to those skilled in the art. In general, during any of the processes for preparation of the compounds disclosed herein, it may be necessary and/or desirable to protect sensitive or reactive groups on any of the molecules concerned. This may be achieved by means of conventional protecting groups, such as those described in *Protective Groups in Organic Chemistry* (ed. J.F.W. McOmie, Plenum Press, 1973); and P.G.M. Green, T.W. Wutts, *Protecting Groups in Organic Synthesis* (3rd ed.) Wiley, New York (1999), which are both hereby incorporated herein by reference in their entirety. The protecting groups may be removed at a convenient subsequent stage using methods known from the art. Synthetic chemistry transformations useful in synthesizing applicable compounds are known in the art and include e.g. those described in R. Larock, *Comprehensive Organic Transformations*, VCH Publishers, 1989, or L. Paquette, ed., *Encyclopedia of Reagents for Organic Synthesis*, John Wiley and Sons, 1995, which are both hereby incorporated herein by reference in their entirety. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims. Unless otherwise indicated, substituent variables in the following schemes have the same definitions as elsewhere in this application.

An exemplary but non-limiting general synthetic scheme for preparing the intermediate compound of Formula (I) is shown in Scheme 1, below. Unless otherwise indicated, the variable definitions are as above for Formula (I). This process starts with β-hydroxy ester (A), where $R_9$ is selected from the group consisting of optionally substituted $C_1$-$C_{12}$ alkyl, optionally substituted $C_3$-$C_8$ cycloalkyl, optionally substituted $C_2$-$C_{12}$ alkenyl, optionally substituted $C_2$-$C_{12}$ alkynyl, optionally substituted aryl and optionally substituted heteroaryl.

Compound (A) is treated with a base and PG-LG, where PG is a hydroxyl protecting group and LG is a leaving group, to append a protecting group to the alcohol moiety of (A), providing Compound (B). In some embodiments, suitable bases include, but are not limited to, sodium hydride, potassium hydride, triethylamine, diisopropylethylamine, triisopropylamine, piperidine, imidazole, t-butyl magnesium chloride, DBU, DABCO, and potassium t-butoxide. In some embodiments, PG is a trialkylsilyl group, such as a trimethylsilyl or t-butyldimethylsilyl. In some embodiments, PG is an acetal, such as O-methoxymethyl ether or O-tetrahydropyran. In some embodiments, PG is an ether, such as benzyl ether, p-methoxybenzyl ether, or methyl ether. In some embodiments, suitable leaving groups include Cl, Br, I, methanesulfonyl, p-toluenesulfonyl, trifluoromethanesulfonyl, p-fluorophenyl, pentafluorophenyl, or p-nitrosulfonyl.

Compound (B) is subsequently treated with borane (C) and a catalyst, to form boronate (D). In some embodiments, X is selected from the group consisting of substituted or unsubstituted variants of the following: $C_1$-$C_4$ alkyl, $C_2$-$C_4$ alkenyl, and $C_2$-$C_4$ alkynyl In some embodiments, $R_{11}$ is selected from the group consisting of substituted or unsubstituted variants of the following: $C_1$-$C_{12}$ alkyl, $C_2$-$C_{12}$ alkenyl, $C_2$-$C_{12}$ alkynyl, $C_3$-$C_{12}$ cycloalkyl, $C_3$-$C_{12}$ cycloalkenyl, $C_3$-$C_{12}$ cycloalkynyl, $C_3$-$C_{12}$ heterocyclyl, aryl, heteroaryl, arylalkyl, heteroarylalkyl, and (cycloalkyl)alkyl. In some embodiments, $R_{12}$ is selected from the group consisting of substituted or unsubstituted variants of the following: $C_1$-$C_{12}$ alkyl, $C_2$-$C_{12}$ alkenyl, $C_2$-$C_{12}$ alkynyl, $C_3$-$C_{12}$ cycloalkyl, $C_3$-$C_{12}$ cycloalkenyl, $C_3$-$C_{12}$ cycloalkynyl, $C_3$-$C_{12}$ heterocyclyl, aryl, heteroaryl, arylalkyl, heteroarylalkyl, and (cycloalkyl)alkyl. In some embodiments, suitable catalysts include ligand-bound transition metals such as rhodium, iridium, ruthenium, cobalt, nickel, palladium, titanium, and zirconium. In some embodiments, suitable ligands include triphenylphosphine, carbon monoxide, chloride, BINAP, CPhos, Xantphos, 1,5-cyclooctadiene, 1,2-Bis(diphenylphosphino)ethane, 1,2-Bis(diphenylphosphino)propane, 1,2-Bis(diphenylphosphino)butane, 1,1'-Bis(diphenylphosphino)ferrocene, and any combination thereof.

Compound (D) is subsequently exposed to deprotection conditions to remove the protecting group, followed by oxidation, affording cyclic boronic acid (E). In some embodiments, suitable deprotection conditions include treatment with acid, such as HF, HCl, HBr, p-toluenesulfonic acid, methanesulfonic acid, acetic acid, or trifluoroacetic acid. In some embodiments, suitable deprotection conditions with acid include aqueous acid. In some embodiments, suitable deprotection conditions include treatment with base, such as NaOH, KOH, sodium hydride, potassium hydride, t-butyl magnesium chloride, LDA, and potassium t-butoxide. In some embodiments, suitable deprotection conditions include treatment with a reducing agent, such as $H_2$, Ni○, Pdo, Na/NH₃. In some embodiments, suitable deprotection conditions include treatment with an oxidizing agent, such NaIO₄. In some embodiments, suitable deprotection conditions include hydrogenation, for example with Pd/C and H₂ or Raney nickel and H₂. In some embodiments, suitable deprotection conditions include hydride abstraction, for example, with DDQ or Ph₃CBF₄. In some embodiments, suitable deprotection conditions include treatment with a Lewis acid, such as BBr₃ or Me₃SiI. In some embodiments, suitable deprotection conditions include treatment with a nucleophile, such as EtSNa or LiI. In some embodiments, suitable deprotection conditions include combinations of the above listed embodiments (e.g aqueous acid followed or together with NaIO₄ oxidation.

Compound (E) is then treated with complexing group (F) to form a compound of Formula (I). In some embodiments, Compound (E) and complexing group (F) are dissolved in a suitable solvent or combination of solvents. In some embodiments, a suitable solvent is, for example, dimethyl ether, diethyl ether, diisopropyl ether, MTBE, ACN, THF, DCM, chloroform, ethyl acetate, pentanes, hexanes, heptanes, petroleum ether, benzene, toluene, trifluorotoluene, acetone, 2-Me-THF, CPME,2-butanone 1,2-dichloroethane, dioxane, pyridine, o-xylene, m-xylene, p-xylene, or any combination thereof.

In some embodiments, the solvent is an ethereal solvent such as dimethyl ether, diethyl ether, diisopropyl ether, MTBE or dioxane. In some embodiments, the solvent is a mixture of an ethereal solvent such as dimethyl ether, diethyl ether, diisopropyl ether, MTBE or dioxane and another solvent selected from heptane, hexanes, ethyl acetate, toluene or ACN. In some embodiments the ethereal solvent is MTBE. In some embodiments, the ethereal solvent is dioxane. In some embodiments, solvent is a mixture of MTBE and ACN. In some embodiments, the solvent is a mixture of MTBE, ACN and heptane. In some embodiments, the solvent is a mixture of MTBE and dioxane. In some embodiments, the ratio of MTBE to ACN is between 5 to 1 and 10 to 1. In some embodiments the ratio of MTBE to ACN is between 6 to 1 and 7 to 1.

In some embodiments, n is 0 or 1. In some embodiments, $Y_1$ is O. In some embodiments, $Y_1$ is $N^+R_5R_6$. In some embodiments, $Y_2$ is O. In some embodiments, $Y_2$ is $NR_{10}$. In some embodiments, $R_1$, $R_2$, $R_3$, $R_4$, $R_5$, $R_6$, and $R_{10}$ are independently selected from the group consisting of H, optionally substituted phenyl and optionally substituted $C_{1-4}$ alkyl. In some embodiments, Compound (F) is ethanolamine. In some embodiments, Compound (F) is glycine. In some embodiments, Compound (F) is oxalic acid. In some embodiments, Compound (F) is glycolic acid.

Scheme 1

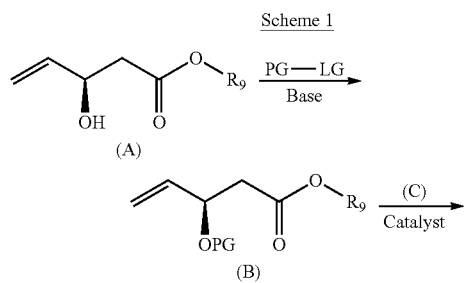

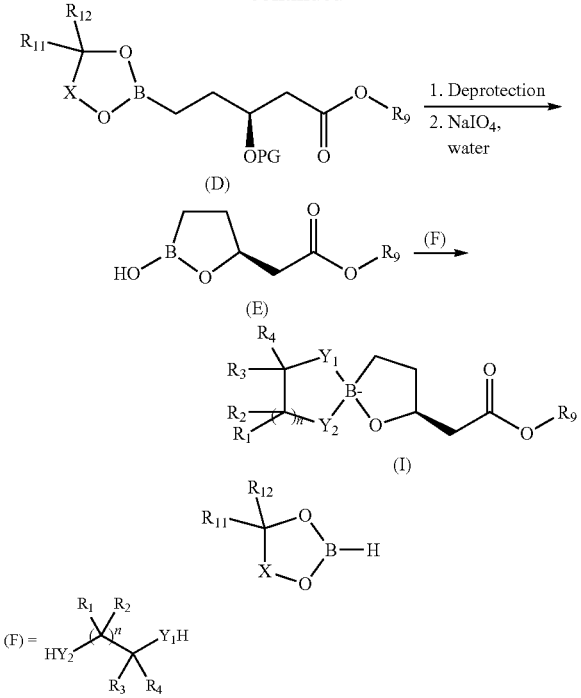

The intermediate compound of Formula (I) can be crystallized and isolated. One skilled in the art will recognize that specific crystallization conditions will depend, in part upon the identities of the particular substituents in each molecule, for example $R_1$, $R_2$, $R_3$, $R_4$, $R_5$, $R_6$, and/or $R_9$. Crystallization occurs in a suitable solvent or solvent system at a particular temperature or range of temperatures. In some embodiments, suitable solvents include dimethyl ether, diethyl ether, diisopropyl ether, MTBE, ACN, THF, DCM, chloroform, ethyl acetate, pentanes, hexanes, heptanes, petroleum ether, benzene, toluene, trifluorotoluene, acetone, 2-Me-THF, CPME, 2-butanone, 1,2-dichloroethane, dioxane, pyridine, o-xylene, m-xylene, p-xylene, or any combination thereof. In some embodiments, suitable temperatures include no higher than −25° C., no higher than −20° C., no higher than −15° C., no higher than −10° C., no higher than −5° C., no higher than 0° C., no higher than 5° C., no higher than 10° C., no higher than 15° C., no higher than 20° C., no higher than 25° C., no higher than 30° C.

In some embodiments, the compound of Formula (I) can be crystallized in a mixture of acetonitrile and MTBE. In some embodiments this mixtures is at least 5% MTBE, at least 10% MTBE, at least 15% MTBE, at least 20% MTBE, at least 25% MTBE, at least 30% MTBE, at least 35% MTBE, at least 40% MTBE, at least 45% MTBE, at least 50% MTBE, at least 55% MTBE, at least 60% MTBE, at least 65% MTBE, at least 70% MTBE, at least 75% MTBE, at least 80% MTBE, at least 85% MTBE, at least 90% MTBE, or at least 95% MTBE. In some embodiments, the compound of Formula (I) heptane is added to the mixture of MTBE and ACN. In some embodiments, these mixtures of MTBE and ACN contain at least 5% heptane, 10% heptane, at least 15% heptane, at least 20% heptane, at least 25% heptane, at least 30% heptane, at least 35% heptane, at least 40% heptane, at least 45% heptane, at least 50% heptane, at least 55% heptane, at least 60% heptane, at least 65% heptane, at least 70% heptane, at least 75% heptane, at least 80% heptane, at least 85% heptane, at least 90% heptane, or at least 95% heptane. The intermediate compound of Formula (I) can be used to synthesize therapeutic boronate beta-lactamase inhibitors. For example, an exemplary but non-limiting general synthetic scheme for preparing therapeutic boronate compounds from compounds of Formula (I) is shown in Scheme 2, below.

Unless otherwise indicated, the variable definitions are as above for Formula (I). The process starts with decomplexation and protection of the boronate moiety. In some embodiments, decomplexation and protection can be accomplished concomitantly or in separate individual steps.

In some embodiments, the decomplexation and protection of the boronate is accomplished using a concomitant process which entails mixing the compound of Formula (I) and the boronate protecting group in a biphasic solvent system, one aqueous/hydrophilic solvent and an organic solvent. Non-limiting examples include water, with or without acid or base, and MTBE, $CH_2Cl_2$, ethyl acetate, 2-Me-THF, CPME, and diisopropyl ether. This reaction provides protected boronate (I-B).

In some embodiments, the complexing moiety (F) is then removed by phase partitioning, and the protected boronate is isolated as a solution. In some embodiments, the decomplexation and protection of the boronate is accomplished using a step-wise process. In some embodiments, compound of Formula (I) is dissolved in water with or without an acid and the decomplexed boronate is extracted with an organic solvent not miscible with water, such as MTBE, $CH_2Cl_2$, ethyl acetate, 2-Me-THF, CPME, diisopropyl ether. In some embodiments, the protecting-boronate reagent is then added to the organic solution of the decomplexed boronate and the protected boronate (I-B) is then isolated as a solution.

In some embodiments the acid is HCl or $H_2SO_4$. In some embodiments, the organic solvent is MTBE or $CH_2Cl_2$. In some embodiments, the organic solvent is MTBE. In some embodiments, the organic solvent is $CH_2Cl_2$. In some embodiments, the boronate protecting group is a compound of Formula G. In some embodiments, n is 0 or 1. In some embodiments, $R_1$, $R_2$, $R_3$ and $R_4$ are independently selected from the group consisting of H, optionally substituted phenyl, optionally substituted carbocyclyl and optionally substituted $C_{1-4}$ alkyl, or $R_1$ and $R_3$ together with the atoms to which they are attached form a carbocyclic ring.

In some embodiments, n is 0. In some embodiments, n is 1.

In some embodiments, $R_1$, and $R_3$, are phenyl and $R_2$, and $R_4$ are hydrogen. In some embodiments, $R_1$, and $R_3$, are isopropyl and $R_2$, and $R_4$ are hydrogen. In some embodiments, $R_1$, and $R_3$, are cyclohexyl and $R_2$, and $R_4$ are hydrogen.

In some embodiments, the boronate-protecting group is pinanediol, pinacol, 1,2-dicycloethanediol, 1,2-diisopropylethanediol, 1,2-diphenylethanediol. In some embodiments, the boronate-protecting group is pinanediol. In some embodiments, the boronate-protecting group is (+)-pinanediol. In some embodiments, the boronate-protecting group is (−)-pinanediol.

In some embodiments, the compound of Formula I-B is then treated with a base and PG-LG, where PG is a hydroxyl protecting group and LG is a leaving group, to append a protecting group to the alcohol moiety of (I-B), providing Compound (I-C). In some embodiments, suitable bases include, but are not limited to, sodium hydride, potassium hydride, triethylamine, diisopropylethylamine, triisopropylamine, piperidine, imidazole, t-butyl magnesium chloride, DBU, DABCO, and potassium t-butoxide. In some embodiments, PG is a trialkylsilyl group, such as a trimethylsilyl or t-butyldimethylsilyl. In some embodiments, PG is an acetal, such as O-methoxymethyl ether or O-tetrahydropyran. In some embodiments, PG is an ether, such as benzyl ether, p-methoxybenzyl ether, or methyl ether. In some embodiments, suitable leaving groups include Cl, Br, I, methanesulfonyl, p-toluenesulfonyl, trifluoromethanesulfonyl, p-fluorophenyl, pentafluorophenyl, or p-nitrosulfonyl.

Halomethylation of compound of Formula (I-C), at the carbon adjacent to the boron atom affords Compound I-D. In some embodiments, halomethylation is accomplished by treatment with n-butyllithium and dichloromethane. In some embodiments, halomethylation is accomplished with dibromomethane and lithium diisopropylamide or lithium hexamethyldisilazide. In some embodiments, subsequent treatment of Compound I-D with an amine nucleophile displaces the halogen to form an amino group at the alpha position. Exemplary nucleophiles include, but are not limited to lithium hexamethyldisilazide and ammonia. Subsequent reaction with a carboxylic acid containing moiety under amide coupling conditions provides Compound I-E. In some embodiments, amide bond coupling conditions include treatment with EDCl, HOBt, HBTU, HATU, PyBOP, PyBrop, or DCC. In some embodiments, $R_{13}$ is $C_{1-9}$ alkyl. In some embodiments, $R_{13}$ is $C_{1-9}$alkyl-$R_{14}$. In some embodiments, $R_{14}$ is substituted or unsubstituted aryl. In some embodiments, $R_{14}$ is substituted or unsubstituted heteroaryl. In some embodiments, $R_{14}$ is substituted or unsubstituted carbocyclyl. In some embodiments, $R_{14}$ is substituted or unsubstituted heterocyclyl. In some embodiments, $R_{14}$ is thiophene-2-yl.

De-esterification and de-complexation of Compound I-E provides therapeutic boronate I-F. In some embodiments, de-esterification and de-complexation are accomplished in one step. In some embodiments, de-esterification and de-complexation are accomplished in more than one step. In some embodiments, de-esterification and de-complexation are accomplished by treatment with aqueous acid, dioxane, and a boronic acid acid. In some embodiments, the acid is hydrochloric or sulfuric acid. In some embodiments, the acid is hydrochloric acid. In some embodiments, the acid is sulfuric acid. In some embodiments, the boronic acid is isobutyl boronic acid, phenylboronic acid or boric acid. In some embodiments, the boronic acid is isobutylboroic acid. In some embodiments, the boronic acid is phenylboronic acid. In some embodiments, the boronic acid is boric acid. In some embodiments, the de-esterification and de-complexation are accomplished by treatment with sulfuric acid, dioxane and boric acid. In some embodiments, the de-esterification and de-complexation are accomplished by treatment with hydrochloric acid, dioxane and isobutylboronic acid.

Scheme 2

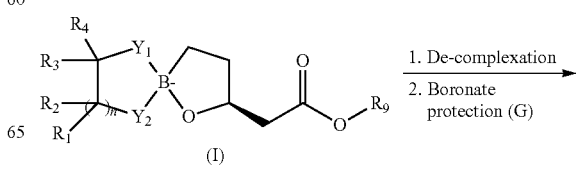

1. De-complexation
2. Boronate protection (G)

(I)

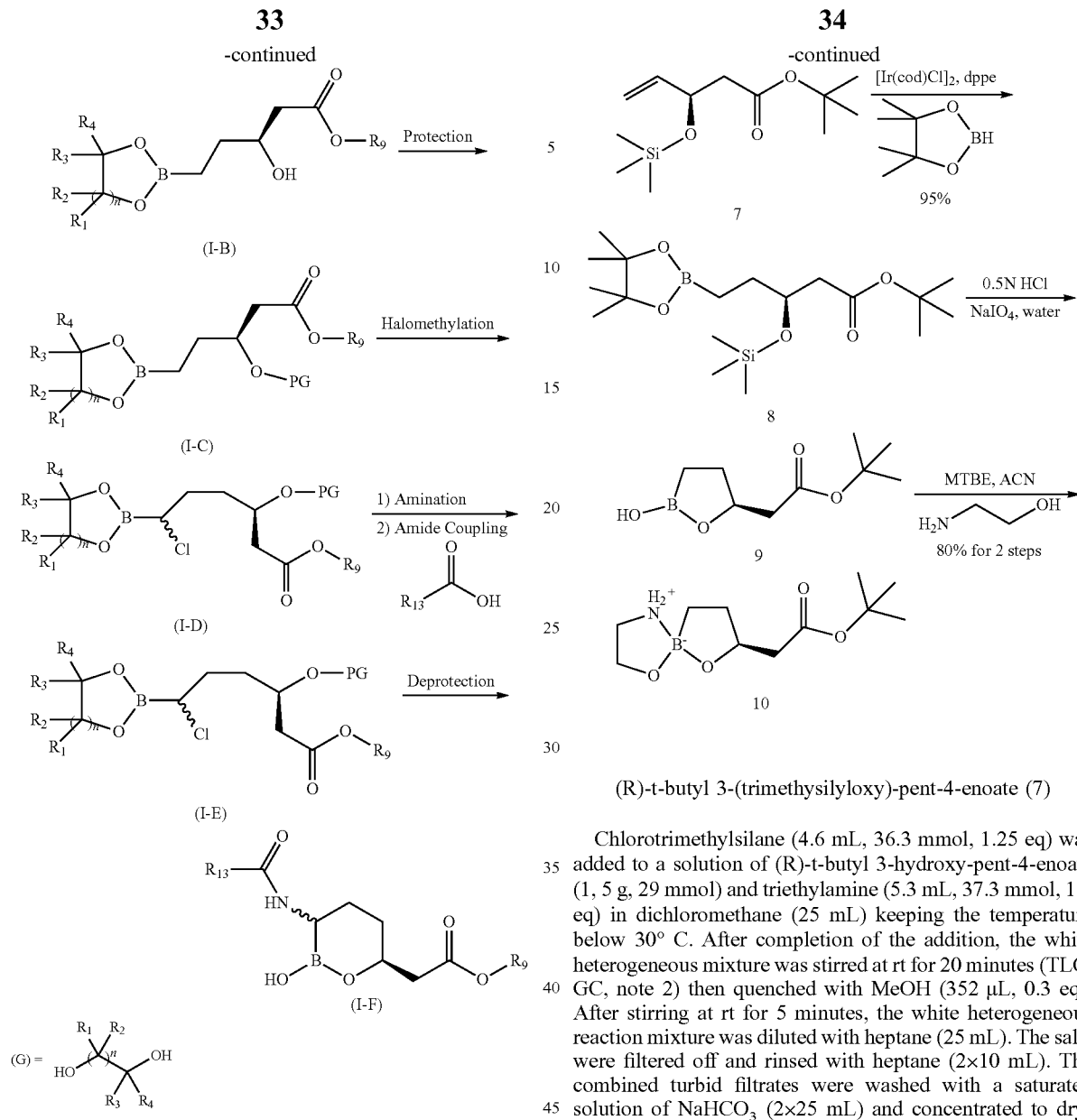

EXAMPLES

Example 1

Synthesis of Intermediate Compound 10

The compound of Formula 10 was synthesized as shown in Scheme 3, below:

Scheme 3

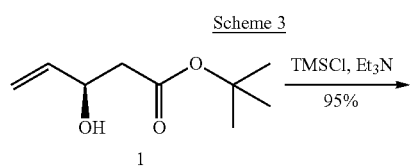

(R)-t-butyl 3-(trimethysilyloxy)-pent-4-enoate (7)

Chlorotrimethylsilane (4.6 mL, 36.3 mmol, 1.25 eq) was added to a solution of (R)-t-butyl 3-hydroxy-pent-4-enoate (1, 5 g, 29 mmol) and triethylamine (5.3 mL, 37.3 mmol, 1.3 eq) in dichloromethane (25 mL) keeping the temperature below 30° C. After completion of the addition, the white heterogeneous mixture was stirred at rt for 20 minutes (TLC, GC, note 2) then quenched with MeOH (352 μL, 0.3 eq). After stirring at rt for 5 minutes, the white heterogeneous reaction mixture was diluted with heptane (25 mL). The salts were filtered off and rinsed with heptane (2×10 mL). The combined turbid filtrates were washed with a saturated solution of NaHCO$_3$ (2×25 mL) and concentrated to dryness. The residual oil was azeotroped with heptane (25 mL) to give a colorless oil that was used immediately.

(S)-t-butyl 3-(trimethylsilyloxy)-5-(4,4,5,5-tetramethyl-[1,3,2]dioxaborolan-2-yl)-pentanoate (8)

A solution of bis-diphenylphosphino-ethane (46.3 mg, 0.2 mol %) and [Ir(COD)Cl]2 (39 mg, 0.1 mol %) in CH2Cl2 (5 mL) was added to a refluxing solution of crude TMS-protected pentenoate 7. Pinacol borane (9.3 mL, 1.1 eq) was added to the refluxing solution. After stirring at reflux for 3 h, the reaction mixture was cooled to room temperature, concentrated to dryness and taken up in heptane (50 mL). The insolubles were filtered over Celite and rinse with heptane (10 mL).

Ethanolamine-boronic acid salt (10)

A mixture of fully protected boronate 8 (5.0 g, 13.4 mmol), 0.5 N HCl (5 mL) and acetone (0.5 mL) was stirred vigorously at room temperature, providing intermediate 9. After complete consumption of the starting material, a solution of NaIO$_4$ (3.44 g, 1.2 eq) in water (15 mL) was added slowly keeping the temperature <30° C. Upon the completion of the addition (30 min), the reaction mixture was allowed to cool to room temperature. After consumption of all pinacol, MTBE (5 mL) was added. After stirring at room temperature for 10 min, the white solids were filtered off and rinsed with MTBE (2×5 mL). The filtrate was partitioned and the aqueous layer was extracted with MTBE (10 mL). The combined organic extracts were washed sequentially with a 0.1 M NaHSO₃ solution (2×5 mL), a saturated NaHCO₃ solution (5 mL) and brine (5 mL). The organic layer was concentrated to dryness. The residue was taken up in MTBE (15 mL) and the residual salts filtered off. The filtrate was concentrated to dryness and the residue was taken up in MTBE (10 mL) and acetonitrile (1.7 mL). Ethanolamine (0.99 mL, 1.1 eq) was added. After stirring at room temperature for 1 hour, the heterogeneous mixture was stirred at 0° C. After stirring at 0° C. for 2 hours, the solids were collected by filtration, rinsed with MTBE (2×5 mL), air dried then dried under high vacuum to give Compound 10 as a white granular powder.

Example 2

Preparation of Beta-Lactamase Inhibitor (15)

The compound of Formula 15 was synthesized as shown in Scheme 4 below:

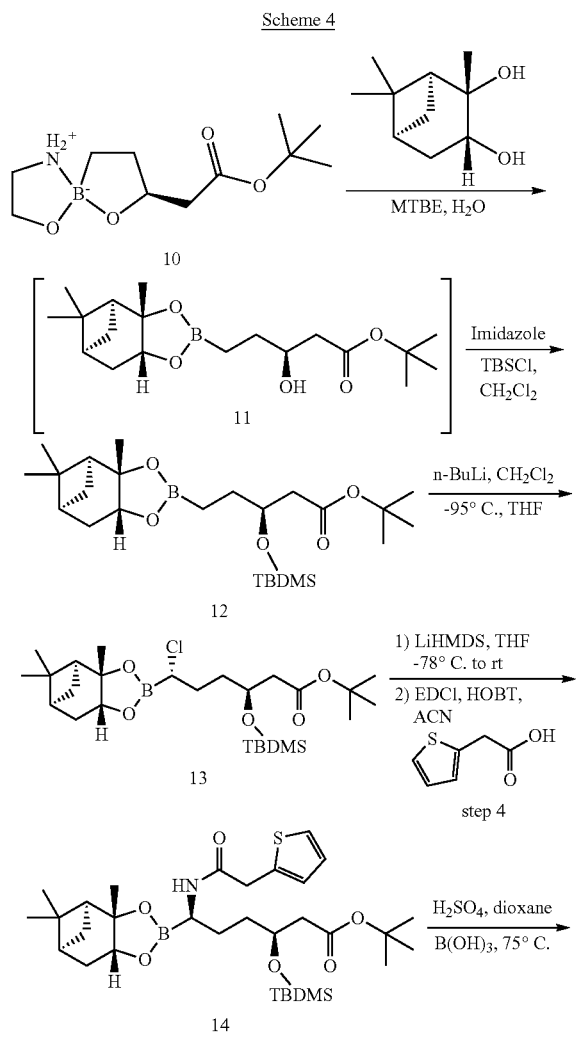

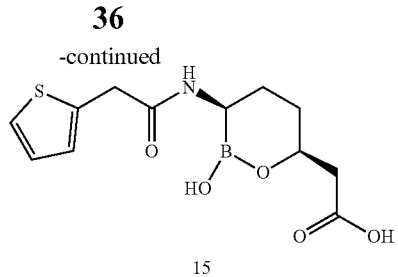

Synthesis of Pinanediol Boronate (12)

Ethanolammonium boronate 11 (15 g, 61.7 mmol) and pinanediol (10.5 g, 61.7 mmol, 1 eq) were suspended in MTBE (75 mL). Water (75 mL) was added and the yellow biphasic heterogeneous mixture was stirred at room temperature. After stirring for 2 hours at room temperature, some pinanediol was still present and stirring was continued overnight. The layers were separated and the organic layer was washed with brine, concentrated under reduced pressure and azeotroped with MTBE (2×30 mL). The residual oil was taken up in dichloromethane (40 mL). In another flask, TBSCl (11.6 g, 77.1 mmol, 1.25 eq) was added to a solution of imidazole (9.66 g, 141.9 mmol, 2.3 eq) in dichloromethane (25 mL). The white slurry was stirred at room temperature. After 5 minutes, the solution of pinanediol boronate was added to the white slurry and the flask was rinsed with dichloromethane (2×5 mL). The heterogeneous reaction mixture was heated at reflux temperature. After stirring at reflux for 8 hours, the reaction mixture was cooled to 30° C. and TMSCl (330 µL) was added. After stirring 30 minutes at 30° C., MeOH (15 mL) was added. After stirring at room temperature overnight, the reaction mixture was washed sequentially with 0.5 N HCl (115 mL), 0.5 N HCl (60 mL) and saturated NaHCO₃ (90 mL). The organic layer was concentrated under reduced pressure and azeotroped with heptane (150 mL) to give 12 as a yellow oil (27.09 g, 94.1%) which was used without purification.

Synthesis of Chloroboronate (13)

A solution of n-butyllithium (2.5 M in hexane, 29.6 mL, 74.1 mmol, 1.3 eq) was added to THF (100 mL) at −80° C. The resulting solution was cooled to −100° C. A solution of dichloromethane (14.6 mL, 228 mmol, 4 eq) in THF (25 mL) was added via syringe pump on the sides of the flask keeping the temperature <−95° C. During the second half of the addition a precipitate starts to appear which became thicker with the addition of the remaining dichloromethane solution. After stirring between −100 and −95° C. for 30 min, a solution of 12 (26.59 g, 57 mmol) in THF (25 mL) was added by syringe pump on the sides of the flask while maintaining the batch temperature <−95° C. to give a clear yellow solution. After stirring between −100 and −95° C. for 30 min, a solution of zinc chloride (1 M in ether, 120 mL, 120 mmol, 2.1 eq) was added keeping the temperature <−70° C. The reaction mixture was then warmed to room temperature (at about −18° C. the reaction mixture became turbid/heterogeneous). After stirring at room temperature for 2 hours, the reaction mixture was cooled to 15° C. and quenched with 1 N HCl (100 mL). The layers were separated and the organic layer was washed sequentially with 1 N HCl (100 mL) and water (2×100 mL), concentrated to oil and azeotroped with heptane (3×150 mL) to provide 13 as a yellow oil (30.03 g, 102%) which was used without purification.

Synthesis of (14)

LiHMDS (1 M in THF, 63 mL, 62.7 mmol, 1.1 eq) was added to a solution of 13 (29.5 g, 57 mmol) in THF (60 mL)

while maintaining the batch temperature at <−65° C. After stirring at −78° C. for 2 hours, additional LiHMDS (5.7 mL, 0.1 eq) was added to consume the remaining starting material. After stirring at −78° C. for 30 minutes, the tan reaction mixture was warmed to room temperature. After stirring at room temperature for one hour, the solution of silylated amine was added via cannula to a solution of HOBT ester of 2-thienylacetic acid in acetonitrile at 0° C. (the solution of HOBT ester was prepared by adding EDCI (16.39 g, 85.5 mmol, 1.5 eq) to a suspension of recrystallized 2-thienylacetic acid (9.73 g, 68.4 mmol, 1.2 eq) and HOBT.H₂O (11.35 g, 74.1 mmol, 1.3 eq) in acetonitrile (10 mL) at 0° C. The clear solution was stirred at 0° C. for 30 minutes prior to the addition of the silylated amine). After stirring at 0° C. for one hour, the heterogeneous reaction mixture was placed in the fridge overnight. Saturated aqueous sodium bicarbonate (80 mL) and heptane (80 mL) were added, and after stirring 30 minutes at room temperature, the layers were separated. The organic layer was washed with saturated aqueous sodium bicarbonate (2×80 mL) and filtered through Celite. The filtrate was concentrated under reduced pressure and the tan oil was azeotroped with heptane (3×110 mL). The residue was taken up in heptane (60 mL) and seeds were added. After stirring at room temperature for one hour, the reaction mixture became heterogeneous. After stirring 4 hours at 0° C., the solids were collected by filtration and washed with ice cold heptane (3×20 mL), air dried then dried under high vacuum to give 14 as an off white powder (10.95 g, 31%).

Synthesis of (15)

A mixture of 14 (10 g, 16.1 mmol), boric acid (1.3 g, 20.9 mmol, 1.3 eq), dioxane (20 mL), and 1 M sulfuric acid (10 mL) was heated at 75° C. After stirring 7 hours at 75° C., the cooled reaction mixture was diluted with water (10 mL) and MTBE (30 mL) and the residual mixture was cooled to 0° C. The pH was adjusted to 5.0 with a solution of 2 N NaOH (14 mL). The layers were separated and the aqueous layer was extracted with MTBE (2×30 mL) then concentrated to dryness. The residue was taken up in water (10 mL) and the solution was filtered through a 0.45 µm GMF syringe filter. The flask and filter were rinsed with water (7.5 mL). The pH of the filtrate was lowered to 4.0 with 2 M H₂SO₄ and seeds (5 mg) were added. After stirring at room temperature for 10 minutes, the pH was lowered to 1.9 over 1 hour with 2 M H₂SO₄ (total volume 3.5 mL). After stirring at room temperature for 2 hours, the solids were collected by filtration. The filtrate was recirculated twice to rinse the flask and the cake was washed with water (2×12 mL), air dried then dried under high vacuum to give 15 as a white powder (3.63 g, 76%).

CONCLUSION

While the invention has been described with reference to the specific embodiments thereof, it should be understood by those skilled in the art that various changes may be made and equivalents may be substituted without departing from the true spirit and scope of the invention. This includes embodiments which do not provide all of the benefits and features set forth herein. In addition, many modifications may be made to adapt a particular situation, material, composition of matter, process, process step or steps, to the objective, spirit and scope of the present invention. All such modifications are intended to be within the scope of the claims appended hereto. Accordingly, the scope of the invention is defined only by reference to the appended claims.

What is claimed is:

1. A compound of Formula (I)

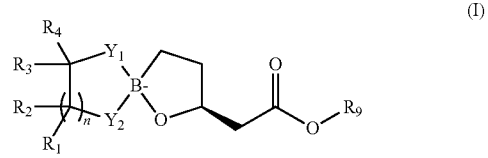

or a salt thereof, wherein:

n is 0 or 1;

$Y_1$ is O or $N^+R_5R_6$;

$Y_2$ is O or $NR_{10}$;

$R_1$ and $R_2$ are independently selected from the group consisting of H, optionally substituted phenyl and optionally substituted $C_{1-4}$ alkyl, or $R_1$ and $R_2$ together with the atoms to which they are attached, form =O;

$R_3$ is selected from the group consisting of H, optionally substituted phenyl, and optionally substituted $C_{1-4}$ alkyl, or $R_3$ and $R_5$, together with the atoms to which they are attached, form a heteroaryl ring; or $R_3$ and $R_4$ together with the atoms to which they are attached, form =O;

$R_4$, $R_5$, $R_6$, and $R_{10}$ are independently selected from the group consisting of H, optionally substituted phenyl, and optionally substituted $C_{1-4}$ alkyl; and $R_9$ is selected from the group consisting of optionally substituted $C_1$-$C_{12}$ alkyl, optionally substituted $C_3$-$C_8$ cycloalkyl, optionally substituted $C_2$-$C_{12}$ alkenyl, optionally substituted $C_2$-$C_{12}$ alkynyl, optionally substituted aryl, and optionally substituted heteroaryl.

2. The compound of claim 1, wherein $Y_1$ is O.

3. The compound of claim 1, wherein $Y_1$ is $N^+R_5R_6$.

4. The compound of claim 1, wherein $Y_2$ is O.

5. The compound of claim 1, wherein $R_1$ and $R_2$ are both H.

6. The compound of claim 1, wherein $R_1$ and $R_2$ together with the atoms to which they are attached, form =O and wherein $R_3$ and $R_4$ together with the atoms to which they are attached, form =O.

7. The compound of claim 1, wherein $R_3$ and $R_4$ are both H.

8. The compound of claim 1, wherein $R_5$ and $R_6$ are both H.

9. The compound of claim 1, wherein $R_9$ is optionally substituted $C_1$-$C_{12}$ alkyl.

10. The compound of claim 1, having a structure selected from the group consisting of:

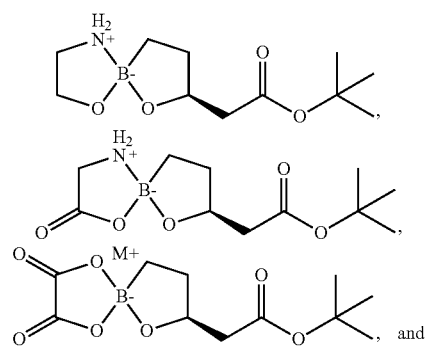

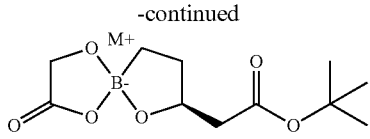

wherein:

M⁺ is a cation selected from the group consisting of lithium, sodium, potassium, calcium, ammonium, triethylammonium, and aluminum.

11. A method of making a compound of Formula (I), or a salt thereof, comprising the steps of:

(a) protecting the hydroxy group of a compound of Formula (A):

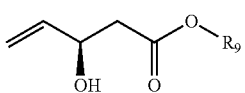

to form a compound of Formula (B):

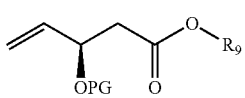

(b) reacting a compound of Formula (B) with a compound of Formula (C):

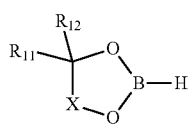

to form a compound of Formula (D):

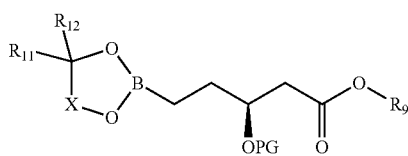

(c) deprotecting a compound of Formula (D) to form a compound of Formula (E):

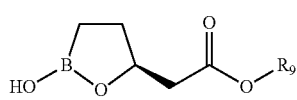

(d) reacting a compound of Formula (E) with a complexing agent of Formula (F):

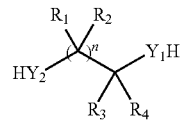

to form a compound of Formula (I):

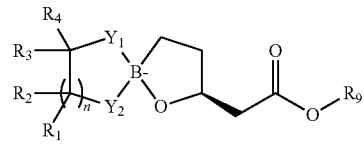

wherein:

PG is a hydroxyl protecting group;

n is 0 or 1;

$Y_1$ is O or $N^+R_5R_6$ $Y_2$ is O or $NR_{10}$;

$R_1$ and $R_2$ are independently selected from the group consisting of H, optionally substituted phenyl, and optionally substituted $C_{1-4}$ alkyl, or $R_1$ and $R_2$ together with the atoms to which they are attached, form =O;

$R_3$ is selected from the group consisting of H, optionally substituted phenyl, and optionally substituted $C_{1-4}$ alkyl, or $R_1$ and $R_3$ together with the atoms to which they are attached form an aryl or heteroaryl ring; or $R_3$ and $R_4$ together with the atoms to which they are attached, form =O;

$R_4$, $R_5$, $R_6$, and $R_{10}$ are independently selected from the group consisting of H, optionally substituted phenyl, and optionally substituted $C_{1-4}$ alkyl;

$R_9$ is optionally substituted $C_1$-$C_{12}$ alkyl, optionally substituted $C_3$-$C_8$ cycloalkyl, optionally substituted $C_2$-$C_{12}$ alkenyl, optionally substituted $C_2$-$C_{12}$ alkynyl, optionally substituted aryl, or optionally substituted heteroaryl;

$R_{11}$ is selected from the group consisting of substituted or unsubstituted variants of the following: $C_1$-$C_{12}$ alkyl, $C_2$-$C_{12}$ alkenyl, $C_2$-$C_{12}$ alkynyl, $C_3$-$C_{12}$ cycloalkenyl, $C_3$-$C_{12}$ cycloalkynyl, $C_3$-$C_{12}$ heterocyclyl, aryl, heteroaryl, arylalkyl, heteroarylalkyl, and (cycloalkyl)alkyl, and X is selected from the group consisting of substituted or unsubstituted variants of the following: $C_1$-$C_4$ alkyl, $C_2$-$C_4$ alkenyl, and $C_2$-$C_4$ alkynyl; and $R_{12}$ is selected from the group consisting of substituted or unsubstituted variants of the following: $C_1$-$C_{12}$ alkyl, $C_2$-$C_{12}$ alkenyl, $C_2$-$C_{12}$ alkynyl, $C_3$-$C_{12}$ cycloalkenyl, $C_3$-$C_{12}$ cycloalkynyl, $C_3$-$C_{12}$ heterocyclyl, aryl, heteroaryl, arylalkyl, heteroarylalkyl, and (cycloalkyl)alkyl.

12. The method of claim 11, wherein $R_1$ and $R_2$ are both H.

13. The method of claim 11, wherein $R_1$ and $R_2$ together with the atoms to which they are attached, form =O and wherein $R_3$ and $R_4$ together with the atoms to which they are attached, form =O.

14. The method of claim 11, wherein $R_3$ and $R_4$ are both H.

15. The method of claim 11, wherein $R_5$ and $R_6$ are both H.

16. The method of claim 11, wherein $R_9$ is optionally substituted $C_1$-$C_{12}$ alkyl.

17. A method of making a compound of Formula (I), or a salt thereof,
comprising the steps of:
reacting a compound of Formula (E):

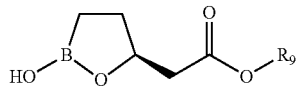
(E)

with a complexing agent of Formula (F):

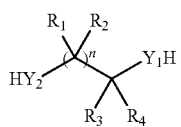
(F)

to form a compound of Formula (I):

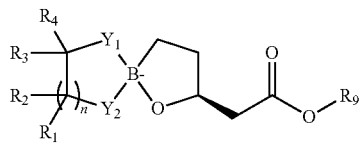

wherein
n is 0 or 1,
$Y_1$ is O or $N^+R_5R_6$
$Y_2$=O or $NR_{10}$,
$R_1$, $R_2$, $R_3$, $R_4$, $R_5$, $R_6$, and $R_{10}$ are independently selected from the group consisting of H, optionally substituted phenyl, and optionally substituted $C_{1-4}$ alkyl; or
wherein independently two geminal $R_1$, $R_2$, $R_3$, $R_4$ together with the atoms to which they are attached, form =O; and
wherein $R_9$ is optionally substituted $C_1$-$C_{12}$ alkyl, optionally substituted $C_3$-$C_8$ cycloalkyl, optionally substituted $C_2$-$C_{12}$ alkenyl, optionally substituted $C_2$-$C_{12}$ alkynyl, optionally substituted aryl or, optionally substituted heteroaryl.

18. The method of claim 17, wherein n is 1.
19. The method of claim 17, wherein $Y_1$ is $N^+R_5R_6$.
20. The method of claim 17, wherein $Y_2$ is $NR_{10}$.
21. The method of claim 17, wherein $R_1$ and $R_2$ are both H.
22. The method of claim 17, wherein $R_3$ and $R_4$ are both H.
23. The method of claim 17, wherein $R_1$ and $R_2$ together with the atoms to which they are attached, form =O and wherein $R_3$ and $R_4$ together with the atoms to which they are attached, form =O.
24. The method of claim 17, wherein $R_5$ and $R_6$ are both H.
25. The method of claim 17, wherein $R_9$ is optionally substituted $C_1$-$C_{12}$ alkyl.
26. The method of claim 17, wherein $R_9$ is t-butyl.

* * * * *